(12) United States Patent
Novogrodsky et al.

(10) Patent No.: US 6,426,366 B1
(45) Date of Patent: Jul. 30, 2002

(54) PHARMACEUTICAL COMPOSITIONS COMPRISING TYRPHOSTINS

(75) Inventors: Abraham Novogrodsky, Rahovot; Alexander Levitzki; Aviv Gazit, both of Jerusalem, all of (IL)

(73) Assignee: Notox, Ltd., Tel Aviv (IL)

( * ) Notice: Subject to any disclaimer, the term of this patent is extended or adjusted under 35 U.S.C. 154(b) by 0 days.

(21) Appl. No.: 09/242,342

(22) PCT Filed: Aug. 14, 1997

(86) PCT No.: PCT/IL97/00276
§ 371 (c)(1),
(2), (4) Date: Apr. 7, 1999

(87) PCT Pub. No.: WO98/06391
PCT Pub. Date: Feb. 19, 1998

(30) Foreign Application Priority Data

Aug. 14, 1996 (IL) .................................. 119069

(51) Int. Cl.$^7$ ............................................ G61K 31/275
(52) U.S. Cl. ........................................ 514/523; 514/525
(58) Field of Search .................................. 514/523, 525

(56) References Cited

U.S. PATENT DOCUMENTS 3,726,662 A 4/1973 Howe et al.

FOREIGN PATENT DOCUMENTS

| DE | 28 00 740 | | 7/1978 | |
| --- | --- | --- | --- | --- |
| EP | 0 322 738 | | 7/1989 | |
| EP | 0 537 949 A1 | | 4/1993 | |
| IL | 27516 | | 4/1971 | |
| IL | 31026 | | 7/1973 | |
| RU | 2024514 | | 12/1994 | |
| WO | 95 02420 A | | 1/1995 | |
| WO | 95/14464 | * | 6/1995 | .................. 514/523 |
| WO | 95 14464 | | 6/1995 | |
| WO | 95 191169 | | 7/1995 | |
| WO | 95 24190 | | 9/1995 | |
| WO | 96 25949 A | | 8/1996 | |
| WO | 97 11692 A | | 4/1997 | |

OTHER PUBLICATIONS

Skinner: "Strategies to prevent nephrotoxicity of anitcancer drugs" Current Opinion in Oncology, 7:310–315, 1995.

Akarasereenont: "The Induction of Cyclo–oxygenase–2 in human Pulmonary Epithelial Cell Culture (A549) Activated by IL–1β Is Inhibited by Tyrosine Kinase Inhibitors" Biochemical and Biophysical Research Communications, vol. 220, No. 1, May 7, 1996, pp. 181–185.

Adamson: "A Phase I trial of Amifostine (WR–2721) and Melphalan in Children with Refractory Cancer" Cancer Research, vol. 55 Sep. 15, 1995, pp. 4069–4072.

Vanichkin: "Late administration of a Lipophilic tyrosine Kinase Inhibitor Prevents Lipopolysaccharide and *Escherichia coli*–Induced Lethal Toxicity" The Journal of Infectious Diseases, vol. 173, No. 4, Apr. 1996, pp. 927–933.

Levitski: "Tyrosine Kinase Inhibition: An Aproach to Drug Development" Science, vol. 267, Mar. 24, 1995, pp. 1782–1788.

Szende: "Tyrphostin induces non–apoptotic programmed cell death in colon tumor cells" Cell biology International, vol. 19, No. 11, 1995, pp. 903–911.

Anderson: "Changes in the survival curve shape of *E. coli* cells following irradiation in the presence of uncouplers of oxidative phosphorylation" Int. J. Radiat. Biol., vol. 48, No. 4, 1985, pp. 495–504.

Gately: "Cisplatin and taxol activate different signal pathways regulating cellular injury–induced expression of GADD153" British Journal Cancer, vol. 73, No. 1, Jan. 1996, pp. 18–23.

Novogrodsky: "Prevention of lipopolysaccharide–induced lethal toxicity by tyrosine kinase inhibitors" Science, vol. 264, No. 5163, May 27, 1994, pp. 1319–1322.

(List continued on next page.)

*Primary Examiner*—Robert Gerstl
(74) *Attorney, Agent, or Firm*—Nath & Associates PLLC; Gary M. Nath; Todd L. Juneau

(57) ABSTRACT

Compounds useful for countering undesired toxic effects to cells, tissues or organs having formula (I) wherein: Ar is a group of formulae (i) or (ii), n is 0 or, when Ar has formula (i) above, then n may also be 1, R is CN, —GC(S)NH$_2$, —C(O)NHR$_3$ or, when R$_1$ is 4-NO$_2$ add R$_2$ is H or 3-OH, then R may also be a group of formulae (iii), (iv), (v), (vi) where R$_3$ is H, phenyl, phenyl(lower alkyl) or pyridylmethyl; R$_1$ and R$_2$ are each independently H, OH, NO$_2$ or, when R is CN, also CH$_3$, F, or CF$_3$, provided that both R$_1$ and R$_2$ are not simultaneously H.

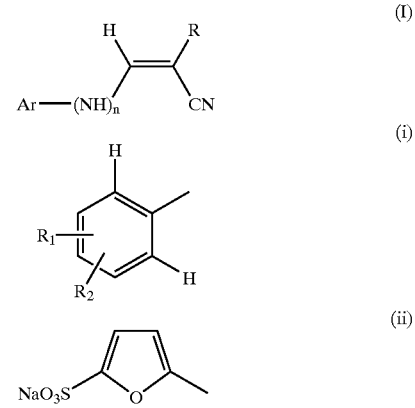

13 Claims, 25 Drawing Sheets

OTHER PUBLICATIONS

Gazit: "Tyrphostins I: Synthesis and biological activity of protein tyrosine kinase inhibitors" *J. Med. Chem.*, vol. 32, No. 19, 1989, pp. 2344–2352.

Lee E. et al., "Selective Inhibition of dexamethasone–induced apoptosis in rat thymocytes by herbimycin A", *Biochem. Biophys. Res. Commun.*, 202(1), pp. 128–134 (1994).

Markovits J. et al., "Inhibition of DNA topoisomerases I and II and induction of apoptosis by erbstatin and tyrphostin derivatives", *Biochem. Pharmacol.*, 48(3), pp. 549–560 (1994).

Krystal GW et al., "Induction of apoptosis and inhibition of small cell lung cancer growth by the quinoxaline tyrphostins", *Cancer Res.*, 57(11), pp. 2203–2208 (1997).

Palumbo GA et al., "The tyrphostin AG17 induces apoptosis and inhibition of cdk2 activity in a lymphoma cell line that overexpresses bcl–2", *Cancer Res.*, 57(12), pp. 2434–2439 (1997).

* cited by examiner

PHARMACEUTICAL COMPOSITIONS COMPRISING TYRPHOSTINS

FIELD OF THE INVENTION

The present invention concerns compositions which are useful to counter damage caused by harmful agents, particularly anti-neoplastic agents used in cancer treatment, e.g. cytotoxic drugs. Damage in the context of the present invention means adverse effects on either cells, tissue or organs. The present invention also concerns therapeutic methods to counter such damage. Furthermore, the present invention concerns also novel compounds useful in such compositions and methods.

BACKGROUND OF THE INVENTION

Most of the commonly used antineoplastic treatments, including chemotherapy and radiation, have adverse toxic effects, manifested on dividing cells and in the function of certain organs. Cells which are particularly affected by such treatment are bone marrow cells, skin cells and cells of the gastrointestinal tract epithelium. In addition, such treatments often cause damage to specific organs, such as the kidney and liver. As a result of such toxic effects, the therapeutic index of such treatments is limited.

It is a long felt want in medical research to try and develop treatment modalities and means which will reduce the unwanted toxic side effects, without affecting the therapeutic activity of the drugs, thus increasing their therapeutic index.

Apoptosis or programmed cell death is a fundamental physiological mechanism of cell death regulated during embryonal development and normal homeostasis mechanisms within the body. Recent data indicated that the anti tumor effect of a variety of chemotherapeutic agents is related to their ability to induce apoptosis. The toxicity of these agents may also be related to the induction of apoptosis in normal cells.

Preliminary reports have described use of various pharmacological agents for the prevention of nephrotoxicity resulting from the use of anti-cancer drugs (Skinner, R., *Current Opinion in Oncology*, 7:310-315, 1995). Attempts were made to counteract the severe chronic proximal tubular toxicity resulting from use of the cytotoxic drug Cisplatin. In in vivo experiments in rats, para-aminobenzoic acid (PABA) co-administered together with cisplatin resulted in reduced nephrotoxicity of the cisplatin without reducing its anti-tumor activity. Other agents such as mitimazole, chloropromazin and L-arginine were also administered to animals in various in vivo experiments carried out in connection with toxicity of cisplatin resulting in only preliminary non-conclusive findings.

The drug amifostine which is dephosphorylated to yield a thiol moiety was also used for reducing anti-toxic effects of anti-neoplastic drugs (*Cancer Res.*, 55:4069, 1995).

GENERAL DESCRIPTION OF THE INVENTION

The present invention provides, by a first of its aspects, a pharmaceutical composition for countering, i.e. reducing or preventing, damage to cells or tissue comprising, as an active agent, an effective amount of a compound of the general formula I:

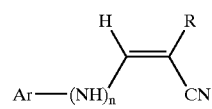

wherein:
Ar is a group of the formulae

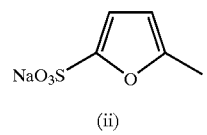

(i)

or

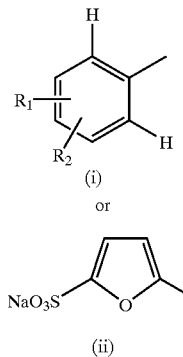

(ii)

n is 0 or, when Ar has the formula (i) above, then n may also be 1,

R is CN, —C(S)NH$_2$, —C(O)NHR$_3$ or, when R$_1$ is 4-NO$_2$ and R$_2$ is H or 3-OH, then R may also be a group of the formula

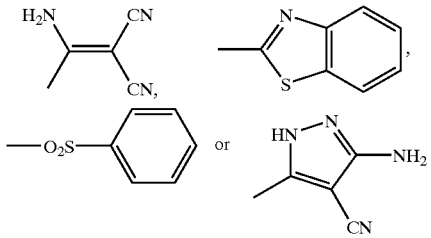

where R$_3$ is H, phenyl, phenyl(lower alkyl) or pyridylmethyl;

R$_1$ and R$_2$ are each independently H. OH, NO$_2$ or, when R is CN, also CH$_3$, F, or CF$_3$, provided that both R$_1$ and R, are not simultaneously H, together with a pharmaceutically acceptable carrier.

Said active agent and said pharmaceutical composition may be administered to or contacted with cells or tissue in a variety of conditions to reduce or prevent undesired damage to cells, tissues or organs. Examples of such conditions are such which may lead to apoptosis. Preventing of undesired apoptosis is a specific embodiment of the invention. Such conditions may also be exposure of said cells, tissue or organ to harmful factors, which may be exogenous or endogenous factors, as well as other physiological conditions, which may lead to damage, e.g. change in temperature, impairment of blood flow, exposure an ionizing irradiation, etc. The damage to be prevented may also be a result of natural physiological deterioration processes, e.g. such occurring( in cells, tissue or organs, maintained, grown or cultured ex vivo.

The present invention also provides a method of treatment of an individual, for countering damage to cells, tissue or organ, comprising administering to the individual an effective amount of a compound having the general formula I.

The term "effective amount" should be understood as meaning an amount of the active compound, which is effective in countering damage manifested in either destruction of normal (non-diseased) cells or damage to a tissue or organ.

The harmful factor may be an exogenous agent e.g., a therapeutic drug having a cytotoxic effect (e.g. antineoplastic drugs), irradiation, noxious chemicals, etc. In addition, the harmful factor may be endogenous, such as free radicals the level of which rises in the course of various metabolic or other disorders, auto-antibodies, cytokines, etc.

The pharmaceutical compositions of the invention may be used in the framework of treatment of various diseases, disorders or conditions such as AIDS, conditions which may give rise to hepatotoxicity, radiation injuries, reducing or inhibiting damage to grafted cells or tissue as a result of graft rejection, for the treatment of intoxications, e.g. paracetamol intoxication, for countering adverse effects of noxious solvents and carriers of therapeutic drugs, countering alcohol-caused damages, etc. Furthermore, the compositions may also be used for countering non-desired immune mediated reactions or an inflammatory response, e.g. septic shock, to reduce damage caused by autoimmune reactions and others. Finally, the pharmaceutical compositions of the invention also may be used- in ex vivo preservation of cells, tissues or organs used for transplantation to reduce or prevent cell or tissue deterioration or death which may otherwise occur during the time they are kept ex vivo prior to transplantation, etc.

The pharmaceutical compositions of the invention are especially useful to counter toxic effects of cytotoxic or anti-metabolic drugs, particularly such as used in cancer therapy. Occasionally, the pharmaceutical composition of the invention will be administered in conjunction with the cytotoxic drug. A pharmaceutical composition according to this embodiment may comprise such a drug in combination with a compound of above formula I.

The compounds of formula I belong to a family of compounds known as Tyrphostin compounds (Levitzki, A. and Gazit, A. *Science*, 267:1782, 1995). In the following text, a compound of Formula I will be referred to as "Tyrphostin" and compositions comprising such compounds will at times be referred to as "Tyrphostin compositions".

Out of the tyrphostins of formula I, some are known, albeit for uses other than those provided by the invention, and others are novel. The novel tyrphostins, which constitute another, independent aspect of the invention, are those of formula I, wherein Ar, $R_1$ $R_2$ and $R_3$ are as defined above, with the provisos that a) R cannot be

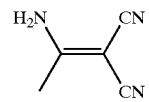

b) when R is CN and n is 0, then
  (ba) if one of $R_1$ and $R_2$ is H or OH, then the other cannot represent $NO_2$;
  (bb) if one of $R_1$ and $R_2$ is H or F, then the other cannot represent H or F; and
c) when $R_1$ is 4-$NO_2$, $R_2$ is H and n is 0, then R cannot represent —C(O)$NH_2$ or —C(S)$NH_2$.

Preferred compounds of formula I for use in the compositions are those wherein R is CN, —C(S)$NH_2$, —C(O)NHCH$_2$C$_6$H$_5$ or a group of the formula

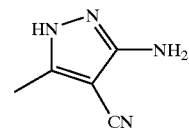

and n is 0, $R_1$ is 4-$NO_2$ and $R_2$ is H.

Examples of tyrphostins are shown in compound Table I. Some of the tyrphostins shown in Compound Table I are novel, and these novel tyrphostins are shown also in Compound Table II.

Compound Table I

| No. | R | R1 | R2 | m.p. °C. | Ref.[1] |
|---|---|---|---|---|---|
| AG1714 | CN | 4-$NO_2$ | H | 153 | 1 |
| AG1791 | ![acetamide] O=C(CH₃)NH₂ | 4-$NO_2$ | H | 238 | 2 |
| AG1744 | ![thioacetamide] S=C(CH₃)NH₂ | 4-$NO_2$ | H | 277 | 3 |
| AG1820 | 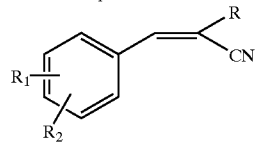 | 4-$NO_2$ | H | 103 | 4 |

-continued

Compound Table I (structure: R1/R2-substituted phenyl-CH=C(R)(CN))

| No. | R | R1 | R2 | m.p. ° C. | Ref.[1] |
|---|---|---|---|---|---|
| AG1822 | CH₃C(O)NH–phenyl | 4-NO₂ | H | 220 | — |
| AG1801 | CH₃C(O)NH–CH₂–phenyl | 4-NO₂ | H | 181 | — |
| AG1824 | CH₃C(O)NH–CH₂–pyridyl | 4-NO₂ | H | 238 | — |
| AG1823 | CH₃C(O)NH–(CH₂)₂–phenyl | 4-NO₂ | H | 187 | — |
| AG1798 | CH₃C(O)NH–(CH₂)₃–phenyl | 4-NO₂ | H | 98 | — |
| AG1745 | CH₃C(O)NH–(CH₂)₄–phenyl | 4-NO₂ | H | 148 | — |
| AG1843 | 3-methyl-5-nitro-4-cyano-1H-pyrazole | 4-NO₂ | H | — | — |
| AG126 | CN | 4-NO₂ | 3-OH | 176 | 5 |
| AG1719 | C(O)NH₂ | 4-NO₂ | 3-OH | 215 | — |
| AG1720 | C(NH₂)=C(CN)₂ (methyl) | 4-NO₂ | 3-OH | 105 | — |
| AG1759 | CN | 4-NO₂ | 3-CH₃ | 97 | — |
| AG1762 | CN | 4-NO₂ | 3-F | 120 | — |
| AG1606 | CH₃C(O)NH–(CH₂)₄–phenyl | 4-NO₂ | 3-OH | 148 | — |

-continued
Compound Table I
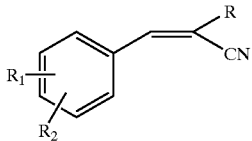
| No. | R | R1 | R2 | m.p. ° C. | Ref.[1] |
|-----|---|----|----|-----------|---------|
| AG1821 | (2-methylbenzothiazole) | 4-NO$_2$ | 3-OH | 178 | 6 |
| AG1781 | CN | 3-NO$_2$ | H | 90 | 10 |
| AG127 | CN | 3-NO$_2$ | 4-OH | 175 | 11 |
| AG178 | CN | 4-F | H | 114 | 11, 12 |
| AG1754 | CN | 3-F | 4-F | 57 | 13 |
| AG1755 | CN | H | 4-CF$_3$ | 95 | — |
| AG1799 | CN | 4-NO$_2$ | O$_2$S-phenyl | 158 | — |
Compound Table II (Novel Compounds)
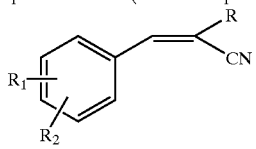
| No. | R | R1 | R2 | m.p. ° C. |
|-----|---|----|----|-----------|
| AG1822 | -C(O)-NH-phenyl | 4-NO$_2$ | H | 220 |
| AG1801 | -C(O)-NH-CH$_2$-phenyl | 4-NO$_2$ | H | 161 |
| AG1824 | -C(O)-NH-CH$_2$-pyridyl | 4-NO$_2$ | H | 238 |
| AG1823 | -C(O)-NH-(CH$_2$)$_2$-phenyl | 4-NO$_2$ | H | 187 |
| AG1798 | -C(O)-NH-(CH$_2$)$_3$-phenyl | 4-NO$_2$ | H | 98 |

-continued

Compound Table II (Novel Compounds)

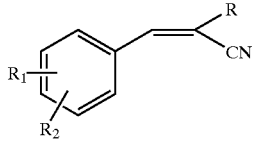

| No. | R | R1 | R2 | m.p. °C. |
|---|---|---|---|---|
| AG1745 | CH₃C(O)NH—(CH₂)₄—phenyl | 4-NO₂ | H | 148 |
| AG1843 | 3-methyl-4-CN-5-NO₂-pyrazole (HN-N) | 4-NO₂ | H | — |
| AG1719 | C(O)NH₂ (acetamide) | 4-NO₂ | 3-OH | 215 |
| AG1720 | H₂N-C(CH₃)=C(CN)₂ | 4-NO₂ | 3-OH | 105 |
| AG1759 | CN | 4-NO₂ | 3-CH₃ | 97 |
| AG1762 | CN | 4-NO₂ | 3-F | 120 |
| AG1606 | CH₃C(O)NH—(CH₂)₄—phenyl | 4-NO₂ | 3-OH | 148 |
| AG1755 | CN | H | 4-CF₃ | 95 |
| AG1799 | CN | 4-NO₂ | O₂S-phenyl | 158 |

LIST OF REFERENCES FOR SEVERAL KNOWN COMPOUNDS USED IN ACCORDANCE WITH THE INVENTION

1. Mowry, D. T., *J. Am. Chem. Soc.,* 67:1050, 1945
2. Zabichy, J., *J. Chem. Soc.,* 683, 1961.
3. Bronskill, J. S., De A., and Ewing, D. F., *J. Chem. Soc. Perkin, Trans. I.,* 629, 1978
4. Junck, H., and Wolny, B., *Moncat. Chem.,* 107:999, 1976
5. Novogrodsky A. Vanichkin, A., Patya, M., Gazit, A., Osherov, N. and Levitzki, A., *Science,* 264:1319, 1994
6. Sakamoto, M., et al., *J. Chem. Soc., Perkin Trans I.,* 1759, 1995
7. 
   (a) Flenner, A. L., C. A. 63:13,278, 1965
   (b) Lythgoe, K., Todd, A. and Tapham, C. *J. Chem. Soc.,* 515, 1944
8. Drabek, J. and Meyer, A., C. A., 89 152,719, 1978
9. Gazit, A., et al., *J. Med. Chem.,* 34:1896, 1991
10. Carson, B. B., and Staughton, R. W., *J. Am. Chem. Soc.,* 50:2825, 1928.
11. Gazit, A., et al., *J. Med. Chem.,* 32:2344, 1989
12. Weinberger, M. A., and Higgin, R. M., *Can. J. Chem.,* 43:2585, 1965
13. Blox Ram, J., Dell, C. P., and Smith, C. W., *Heterocycles,* 38:400, 1994.

Particularly preferred tyrphostins in accordance with the invention are the compounds designated as AG1714, AG1744, AG1801 and AG1843 in the above "Compound Table I". Out of these four compounds, the latter two are novel.

The tyrphostins of formula I may be administered to the patient in combination with another treatment, e.g. in combination with a cytotoxic drug or irradiation. In such a combination treatment the tyrphostins may be administered simultaneously with or at a different time than the other treatment, so as to yield a maximum effect. A particular example is administration of the tyrphostins prior to the other treatment, e.g. several hours prior to the irradiation or to the administration of the cytotoxic drug.

It was found in accordance with the invention that when the tyrphostins of formula I are administered together with another therapeutic agent, they do not reduce the therapeutic activity of the other agent, but rather act in reducing its undesired toxic side effects to normal cells or tissue. This means that the therapy with the therapeutic agent will still achieve the same desired therapeutic effect, at the same dosage. For example, in the case of a chemotherapeutic drug, the administration of a tyrphostin will not, or may only minimally affect the effect of the drug in reducing the tumor load or preventing tumor growth or tumor recurrence, at a given administration dosage. In some cases, however, administration of the tyrphostins even intensifies the therapeutic effect of the treatment. The overall effect of the tyrphostins, in such a combination therapy, is thus the increase in the therapeutic index of another therapy, namely, increase in the ratio between the therapeutic effect of the therapy to its undesired toxic side effects. The increase in therapeutic index may at times be used to advantage of increasing the dosage of the therapeutic agent, e.g. the dosage of the cytotoxic agent or radiation, without a concurrent increase in undesired toxic side effects.

The tyrphostins according to the invention may be administered either in a single dose or may be given repetitively over a period of time, e.g. prior, during and after the treatment with a cytotoxic agent or irradiation.

A preferred mode of administration of the tyrphostins to humans is intravenously, although by a proper formulation, they may also be administered by other administration modes, c.g. intramuscularly, intraperitoneally or orally.

While the tyrphostin compositions will typically contain a single tyrphostin compound, it is possible at times to include in the composition and or co-administer two or more tyrphostins which act together in a synergistic or additive manner to counter damages caused, e.g. by a therapeutic treatment.

BRIEF DESCRIPTION OF THE FIGURES

FIG. 7 is a photograph showing histopathological analysis of kidneys (FIGS. 7A–C) and small intestines (FIGS. 7D–F) of mice administered with cisplatin alone or with the tyrphostin AG1714 prior to the administration of cisplatin. Final magnification ×400:

FIG. 7F—a small intestine of mice treated with AG1714 prior to cisplatin administration showing normal small intestine structure;

FIG. 13 is a graphic representation showing the number of nucleated cells in bone marrow of mice treated with doxorubicin alone or with AG1714 and doxorubicin:

PREPARATIVE EXAMPLES

Figures 1A, 1B:
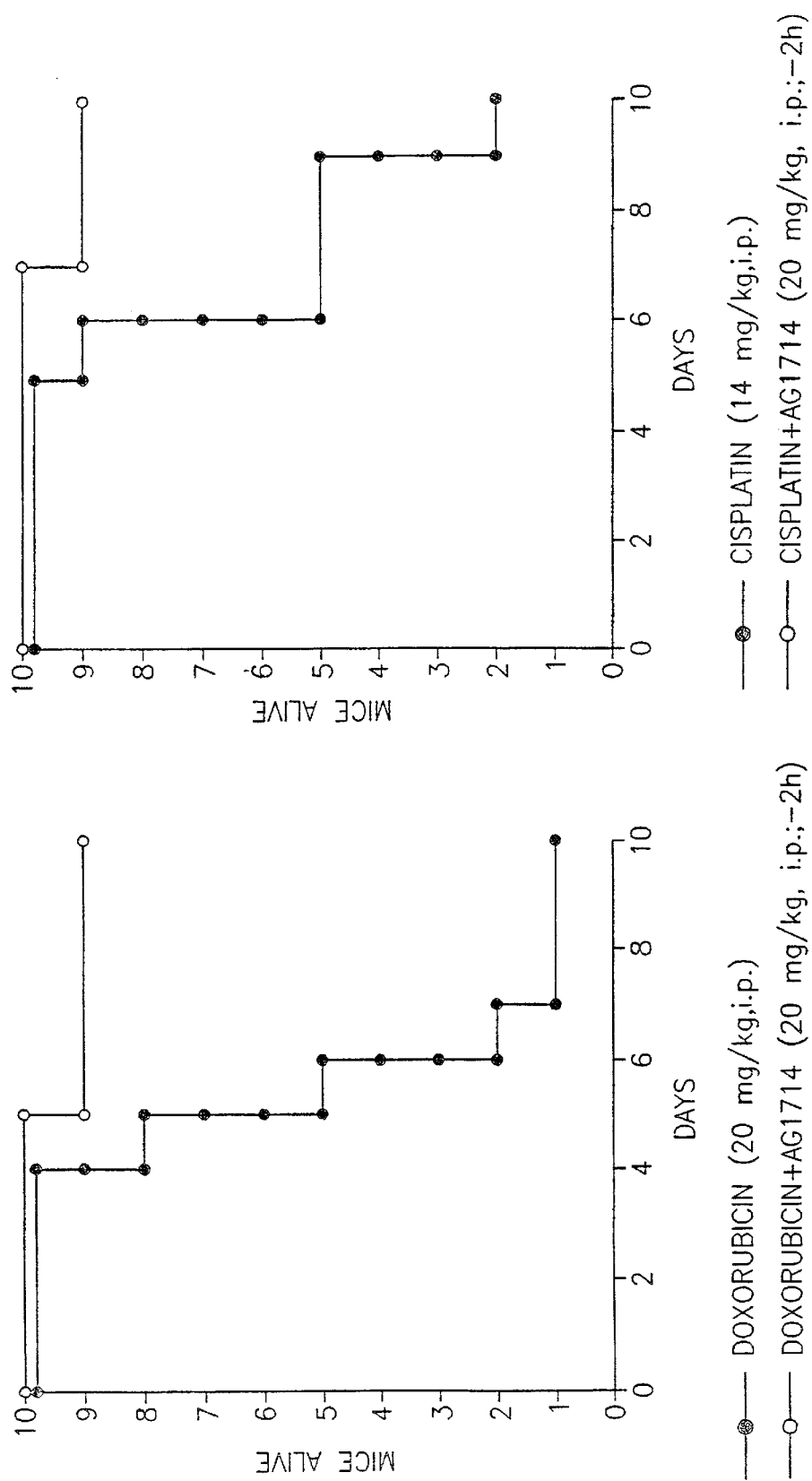
FIG. 1A is a graphic representation showing the mortality of mice treated with doxorubicin as compared to the mortality of mice receiving a single injection of AG1714 two hours before treatment with doxorubicin.
FIG. 1B is a graphic representation showing the mortality of mice treated with cisplatin as compared to the mortality of mice receiving a single injection of AG1714 two hours before treatment with cisplatin.

The preparation of several of the above novel compounds is exemplified in the following preparative examples. In all the examples below, the new compounds were synthesized by knoevenagel condensation of the aldehyde with malononitrile or the substituted amide.

Example 1

AG1801

0.45 g, 3 mM, p-nitro benzaldehyde, 0.61 g, 3.5 mM, N-(Cyano acetyl) benzyl amide (reference 9) and 50 mg β-alanine in 20 ml ethanol were refluxed for 5 hours. Cooling, and filtering gave 0.67 g, 73% yield, light yellow solid, mp-164°. NMR(CDCl$_3$) δ 8.44 (1H,S,vinyl), 8.35, 8.07 (4H,AB, J$_{AB}$=8.8 Hz), 7.35 (5H,m), 6.6(1H,br.t,NH), 4.63(2H,d,J=5.8 Hz).

MS-m/e 307(M$^+$, 50%), 290(M-HCN,63), 260(M—H—NO$_2$,91), 201(M-NHCH$_2$C$_6$H$_5$,15), 173 (M-CONHCH$_2$C$_6$H$_5$, 13), 155(22), 127(21), 105(100).

Example 2

AG1798

0.4 g, 2.65 mM, p-nitrobenzaldehyde, 0.57 g, 2.8 mM, N(cyano acetyl) 3-propyl phenyl amide (reference 9) and 40 mg β-alanine in 30 ml ethanol were refluxed for 4 hours. The solution was concentrated by evaporation, cooled and filtered to give 0.38 g, 43% yield, light-yellow solid, mp-98.

NMR (CDCl$_3$) δ 8.38(1H,S, vinyl), 8.35, 8.06(4H,ABq, J$_{AB}$=8.6 Hz), 7.3(5H,m), 3.50(2H, J=8.0 Hz), 2.74(2H,t,J=8.0 Hz), 2.0 (2H,quintet, J=8.0 Hz).

Example 3

AG 1719

146 mg, 0.87 mM, 3-hydroxy 4-nitro benzaldehyde, 48 mg, 0.89 mM, malononitrile dimer and 20 mg, β-alanine in 10 ml ethanol were refluxed for 1 hour. Evaporation, trituration with CH$_2$Cl$_2$-hexane and filtering gave 190 mg, 78% yield, yellow solid, mp-105. NMR (acetone d$_6$) δ 8.32(1H, d,J=8.6 Hz), 8.20 (1H,S,vinyl), 7.77(1H,d,J=2.2 Hz), 7.65 (1H,dd,J=8.6, 2.2 Hz).

Example 4

AG1762

170 mg, 1 mM, 3-fluoro 4-nitro benzaldehyde, 80 mg, 1.2 mM, malononitrile and 15 mg β-alanine were refluxed for 1 hour. Evaporation, trituration with hexane and filtering gave 202 mg, 93% yield, pink solid, mp-120°. NMR (CDCl$_3$) δ 8.22(1H,m), 7.83(3H,m).

MS-m/c 217(M$^+$, 100), 187(M-NO,78), 171 (M-NO$_2$,19), 159(M-NO—HCN—H,80), 15 1(M-NO$_2$,—HF,33), 144 (M—NO$_2$,—HCN,71), 132(75), 124(M—NO—HCN—HF, 81).

Example 5

AG1799

0.4 g, 2.65 mM, 4-nitro benzaldehyde, 0.51 g, 2.8 mM, phenyl sulphonyl acetonitrile and 40 mg β-alanine in 30 ml ethanol were refluxed for 4 hours. Cooling, filtering and washing with ethanol gave 0.68 g, 82% yield, light yellow solid, mp-158°. NMR (CDCl$_3$) δ 8.36(2H,d,J=8.6 Hz), 8.31 (1H,S, vinyl), 8.07(4H,m), 7.70(3H,m).

Examples of Biological and Therapeutic Activities

The biological and therapeutic effect of some of the compounds which may be used in the composition of the invention will now be exemplified in the following non-limiting examples with occasional reference to the annexed figures.

I. Reduction of Mouse Mortality Caused by Doxorubicin or Cisplatin by Tyrphostins Example 6

6 weeks old female CD1 mice were divided into the following groups:
  i. Mice injected intraperitoneally (i.p.) with doxorubicin (20 mg/kg);
  ii. Mice injected i.p. with cisplatin (14 mg/kg);
  iii. Mice receiving a single i.p. injection of AG1714 (20 mg/kg two hours prior to the doxorubicin; and iv. Mice receiving, a single i.p. injection of AG1714 (20 mg/kg) two hours prior to receiving the cisplatin.

As seen in FIG,. 1, treatment of mice with AG1714 significantly reduced the mortality of the mice as compared to the mortality of mice receiving doxorubicin alone ($p \leq 0.001$) (FIG. 1A) or of mice receiving cisplatin alone ($p \leq 0.005$) (FIG. 1B).

Example 7

6 weeks old female CD1 mice were divided into the following two groups:
i. Mice receiving 10 i.p. injections of doxorubicin at a concentration of 5 mg/kg per each injection over 21 days (cumulative dose of 50 mg/kg); and
ii. Mice receiving 10 i.p. injections of doxorubicin at 5 mg/kg over 21 days with the addition of a single i.p. injection of AG1714 (5 mg/kg) two hours prior to each doxorubicin injection.

Each group consisted of 10 mice and the % mortality in each group was tested as explained above.

Figure 2:
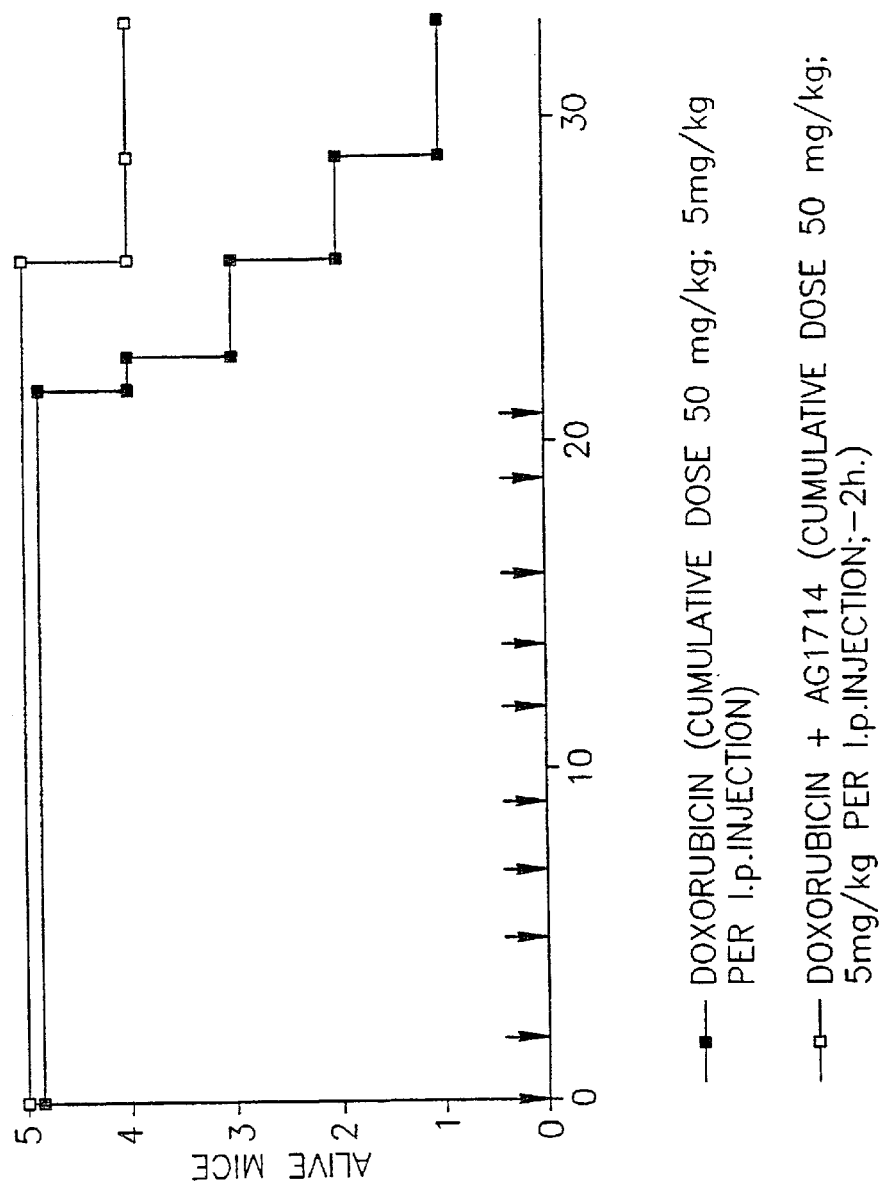
FIG. 2 is a graphic representation showing the mortality of mice receiving 10 i.p. injections of doxorubicin (5 mg/kg) for a period of 21 days (cumulative dose 50 mg/kg) as compared to the mortality of mice treated as above but receiving an i.p. injection of AG1714 (5 mg/kg) two hours prior to each doxorubicin injection.
Figure 3:
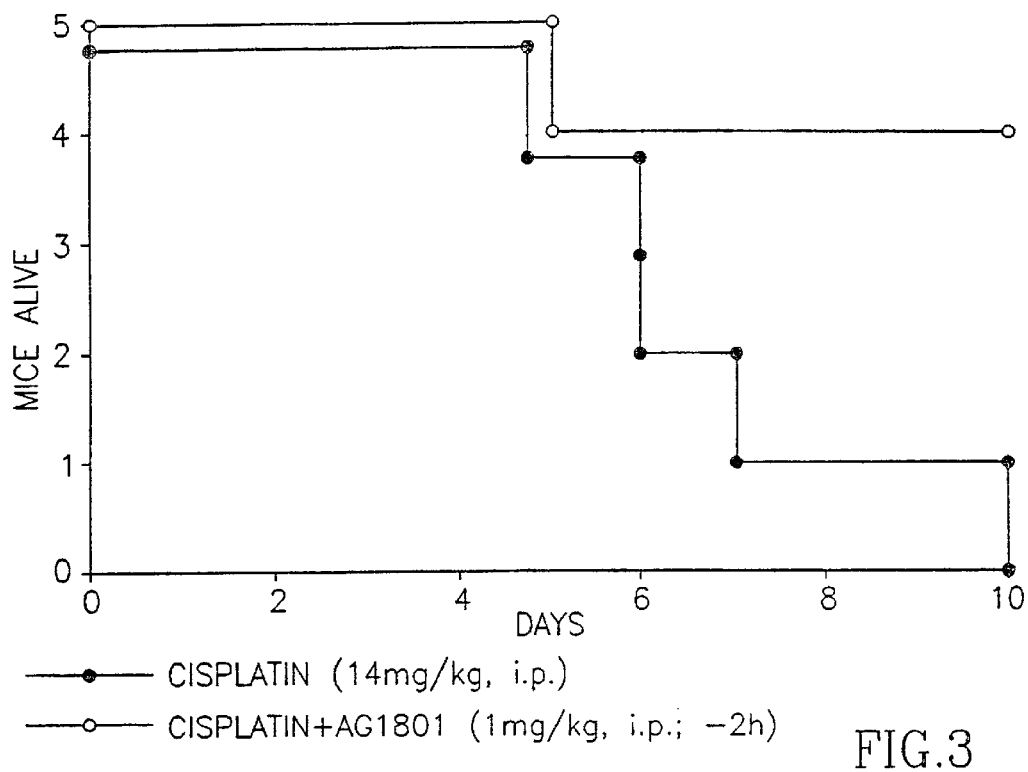
FIG. 3 is a graphic representation showing the mortality of mice treated with cisplatin alone or with cisplatin and AG 1801 over a period of ten days after cisplatin administration.
Figure 4:
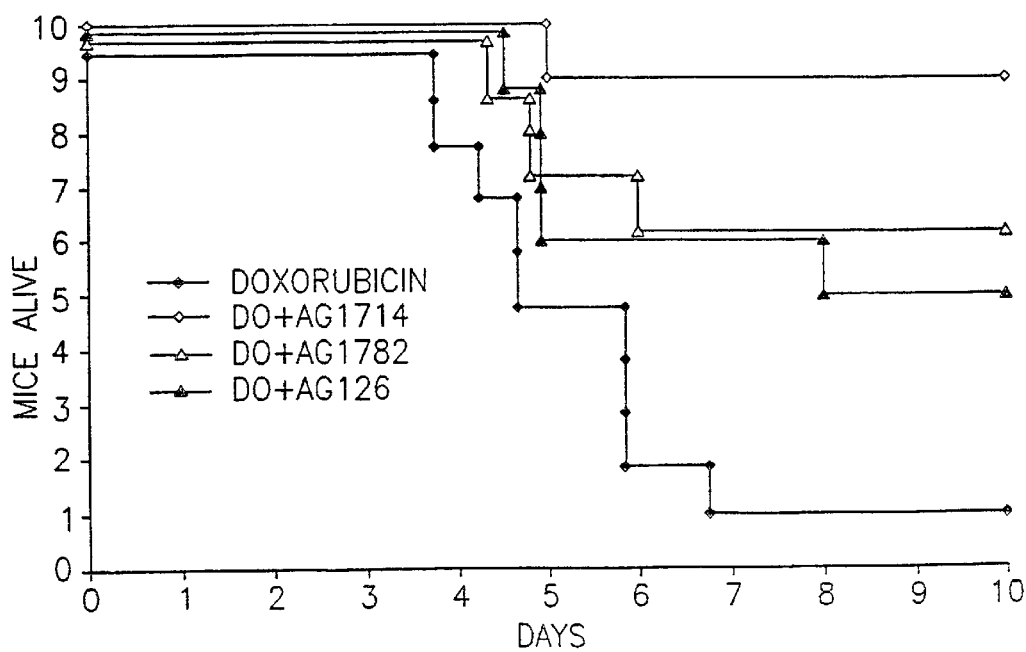
FIG. 4 is a graphic representation showing the mortality of mice treated with doxorubicin alone or with tyrphostins and doxorubicin over a period of ten days after doxorubicin administration.

As seen in FIG. 2, the mortality of the mice receiving injections of AG1714 prior to each administration of doxorubicini was significantly reduced as compared to the high mortality of the mice receiving doxorubicin treatment alone.

Example 8

Two groups of CD1 mice were injected with 14 mg/kg of cisplatin as described above. One group received a single i.p. injection of AG1801 at a low dose of 1 mg/kg two hours before receiving the cisplatin injection. As seen in FIG. 2, all the mice in the group receiving cisplatin alone died within ten days of the injection. Against this, in the group of mice receiving a single injection of AG1801 at a low dose prior to the cisplatin injection, the % mortality was only 20%.

Example 9

CD1 mice were divided into the following five groups:
i. Mice receiving, a single i.p. injection of 20 mg/kg of doxorubicin;
ii. Mice receiving a single i.p. injection of 20 mg/kg of AG1714 and two hours later an i.p. injection of 20 mg/kg of doxorubicin;
iii. Mice receiving a single i.p. injection of 20 mg/kg of AG1782 and two hours later an i.p. injection of 20 mg/kg of doxorubicin;
iv. Mice receiving a single i.p. injection of 20 mg/kg of AG126 and two hours later an i.p. injection of 20 mg/kg of doxorubicin.

The % mortality in each of the above groups was determined by scoring the number of dead mice every day until 10 days after injection.

Figure 10:
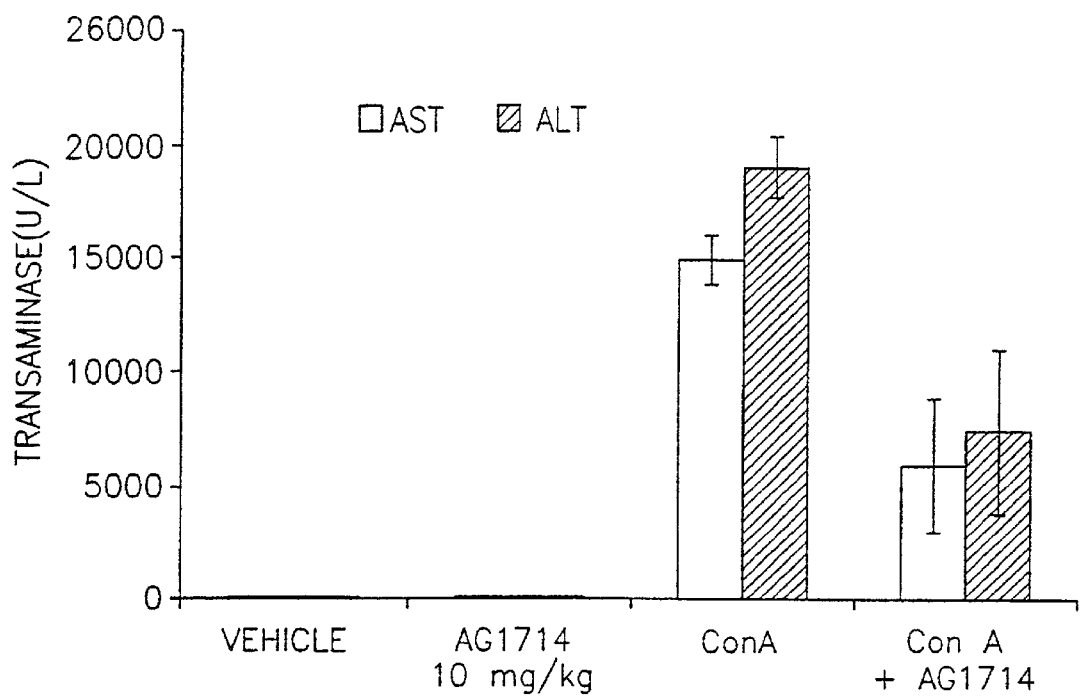
FIG. 10 is a graphic representation showing the level of AST and ALT in serum of mice treated with Con A alone or in combination with AG1714.

As seen in FIG. 10, in the group of mice receiving, doxorubicin alone (i), 90% of the mice were dead within a week after injection. In the other groups of mice receiving the tyrphostins before the administration of doxorubicin, the % mortality was reduced to between 50% (iii) to only 10% (ii).

II. Reduction of the Toxic Effect of Various Harmful Agents on Organs (Kidneys, Liver, Intestines, Heart) of Treated Mice by Tyrphostins Example 10

Groups of CD1 mice, each comprising three mice, were injected i.p. with a dose of 14 mg/kg of cisplatin. The mice in each of the groups except for one were injected with a single i.p. injection an tyrphostin at a dose of 10 mg/kg two hours prior to the injection of the cisplatin. In order to assess the toxic effect of cisplatin on the kidneys of the treated mice (nephrotoxicity), the level of creatinine was determined in the serum of each mouse four days after administration of the cisplatin using a commercial kit by Sigma.

Figure 5:
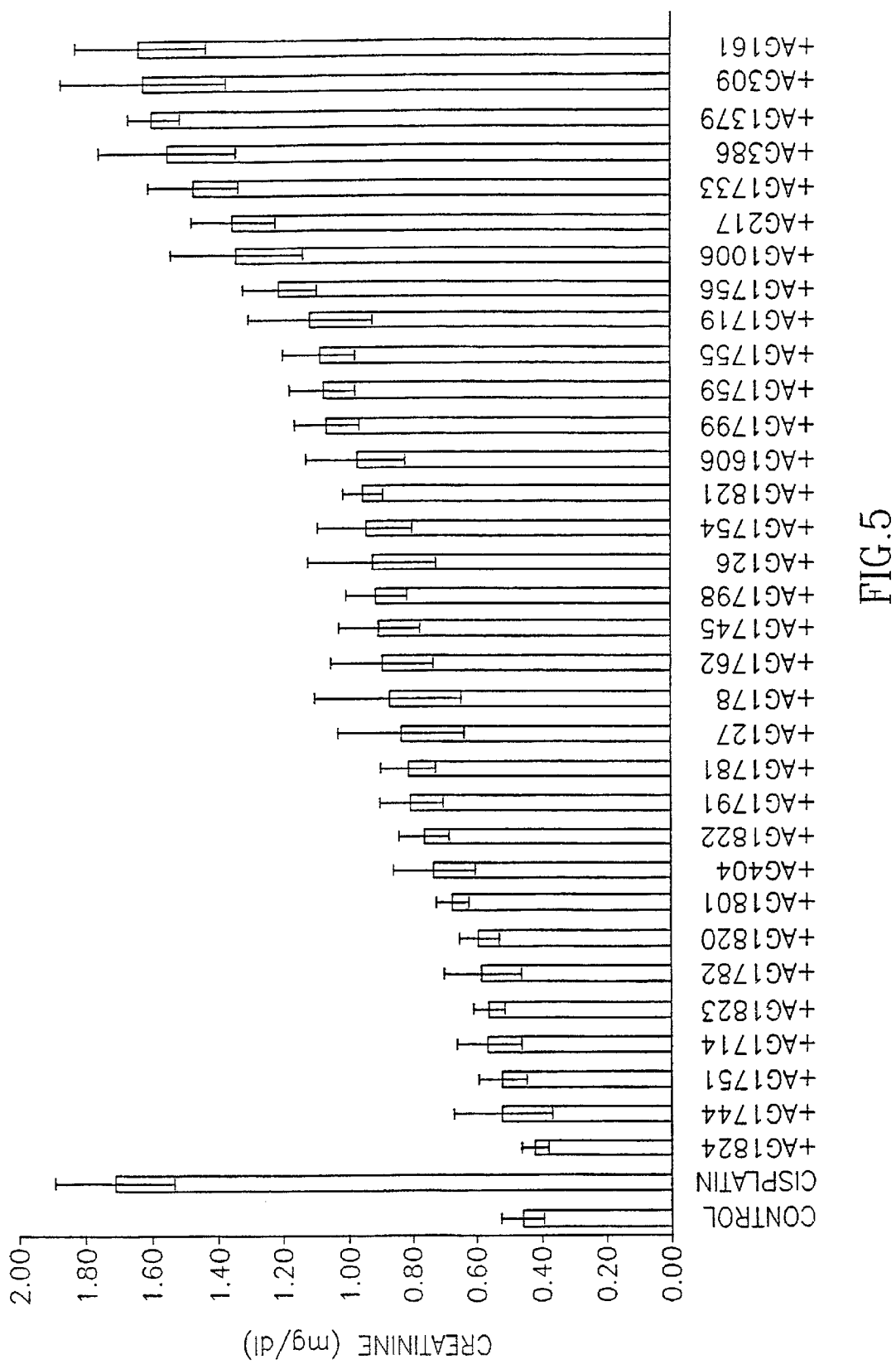
FIG. 5 is a graphic representation showing the effect of a number of tyrphostins on the toxic effect of cisplatin in kidneys of treated mice. The toxic effect is measured by the level of creatinine detected in the serum of the treated mice, a high level of creatinine indicating kidney damage (nephrotoxicity).

As seen in FIG. 5, the creatinine level of about 2 mg/dl detected in the serum of mice receiving cisplatin alone, indicates that there is about a 50% reduction in the kidney function of these mice. Against this, the level of creatinine measured in the serum of many of the mice receiving an injection of an tyrphostin before the cisplatin injection, was lower than the creatinine levels in the serum of mice receiving cisplatin alone. This indicates that injection of the tyrphostins prior to the cisplatin injection reduces the toxic effect of cisplatin on kidney function. The reducing effect on the nephrotoxicity of cisplatin varied between the different tyrphostins. For example, AG1824, AG1744, AG1751, AG1714, AG1823, AG1782, AG1801, markedly reduced the nephrotoxicity of cisplatin bringing the creatinine levels in the serum to those of control mice.

Example 11

CD1 female mice were injected either with cisplatin alone or with a single injection comprising either the tyrphostin AG1843 or AG1714 two hours before injection of cisplatin and the level of the creatinine in their serum was tested as explained above.

As seen in Table I below and in agreement with the results of Example 10 above, cisplatin alone had a nephrotoxic effect on the mice as seen by their high serum creatinine levels (1.53). This toxic effect of cisplatin was significantly reduced (to between 0.45–0.70) by injecting the tyrphostins two hours before cisplatin injection. In this example, the effect of tyrphostin AG1843 administered at a low dose (5 mg/kg) was more effective than the administration of a high dose (20 mg/kg) of the same tyrphostin.

TABLE 1

| Groups | Creatinine mg/dl (mean ± SD) |
|---|---|
| Control (Cosolvent) | 0.46 ± 0.01 |
| Cisplatin 14 mg/kg i.p. | 1.53 ± 0.04 |
| AG1843 5 mg/kg i.p. (−2h) + Cisplatin | 0.45 ± 0.06 |
| AG1843 20 mg/kg (−2h) + Cisplatin | 0.70 ± 0.14 |
| AG1714 20 mg/kg (−2h) + Cisplatin | 0.58 ± 0.06 |

Example 12

CD1 mice were injected (i.p.) with cisplatin (14 mg/kg) or first with AG1714 (10 mg/kg) and two hours after with cisplatin as explained above. Mice in the control croup received injections of the vehicle only (a stock solution of ethanol: chemaphore (50:50) diluted with saline). Four days after administration of the cisplatin, several parameters indicating nephrotoxicity and liver injury were measured in the serums of each of the mice 4 days after cisplatin administration. The parameters showing nephrotoxicity of cisplatin were creatinine and blood urea nitrogen (BUN) and the parameters indicating damage to the liver were the hepatic transaminases alanine-transaminase (ALT) and aspartic transaminase (AST) measured by standard methods. Each group consisted of three mice and the results are shown as mean levels of the measured parameter±SD.

Figures 6A, 6B:
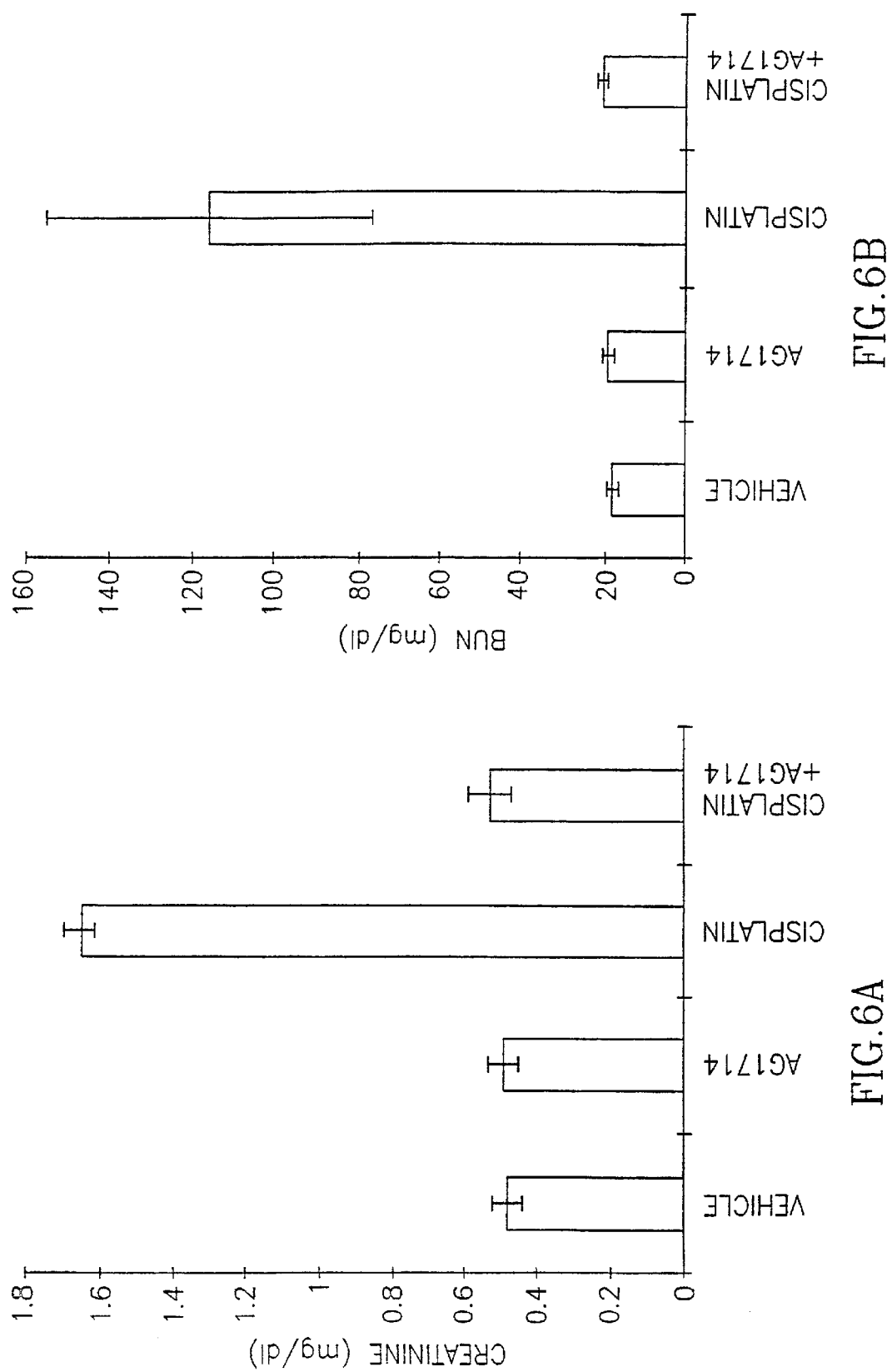
FIG. 6 is a graphic representation showing the level of creatinine (FIG. 6A) and blood urea nitrogen (BUN) (FIG. 6B) (which are indicative of nephrotoxicity) in serum of mice receiving either cisplatin alone, AG1714 alone or a combination of cisplatin and AG1714. The levels of creatinine and BUN were compared to the levels of the same substances in serums of control mice receiving the vehicle only.
Figure 7A:
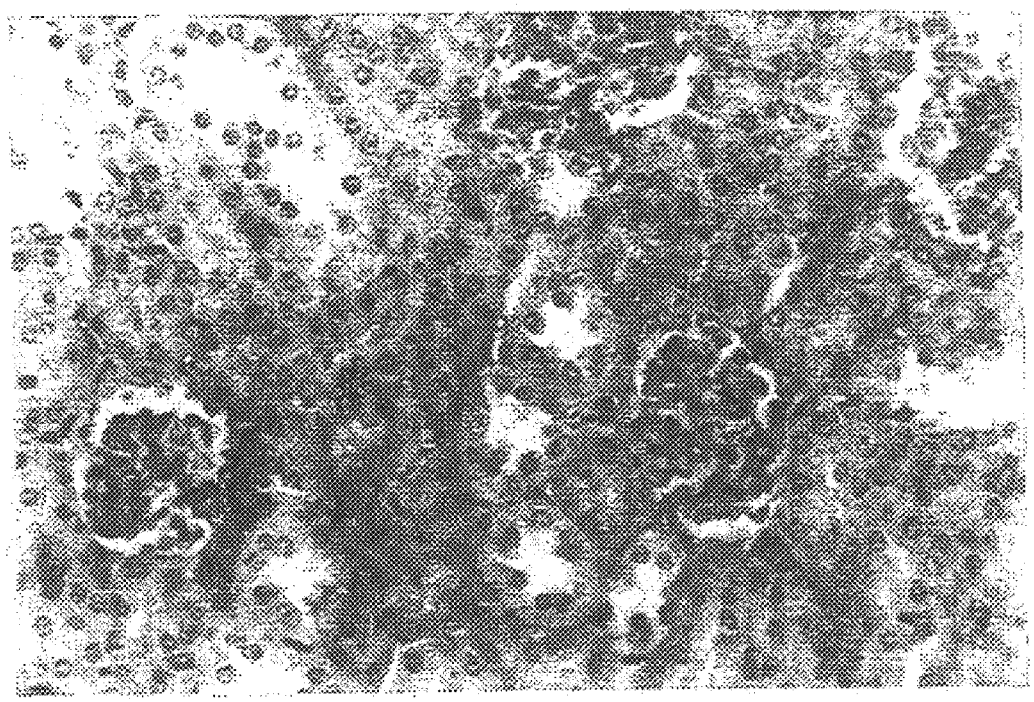
FIG. 7A—kidneys of normal non-treated mice.
Figure 7B:
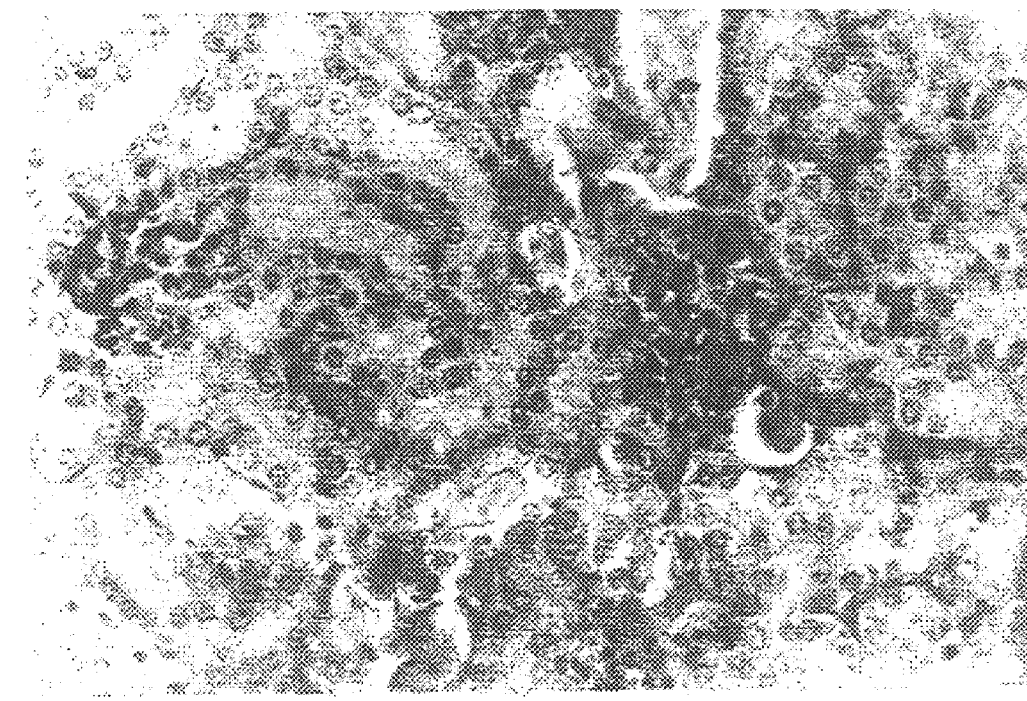
FIG. 7B—kidneys of mice receiving cisplatin alone showing large proteinaceous plaques in the proximal tubules.
Figure 7C:
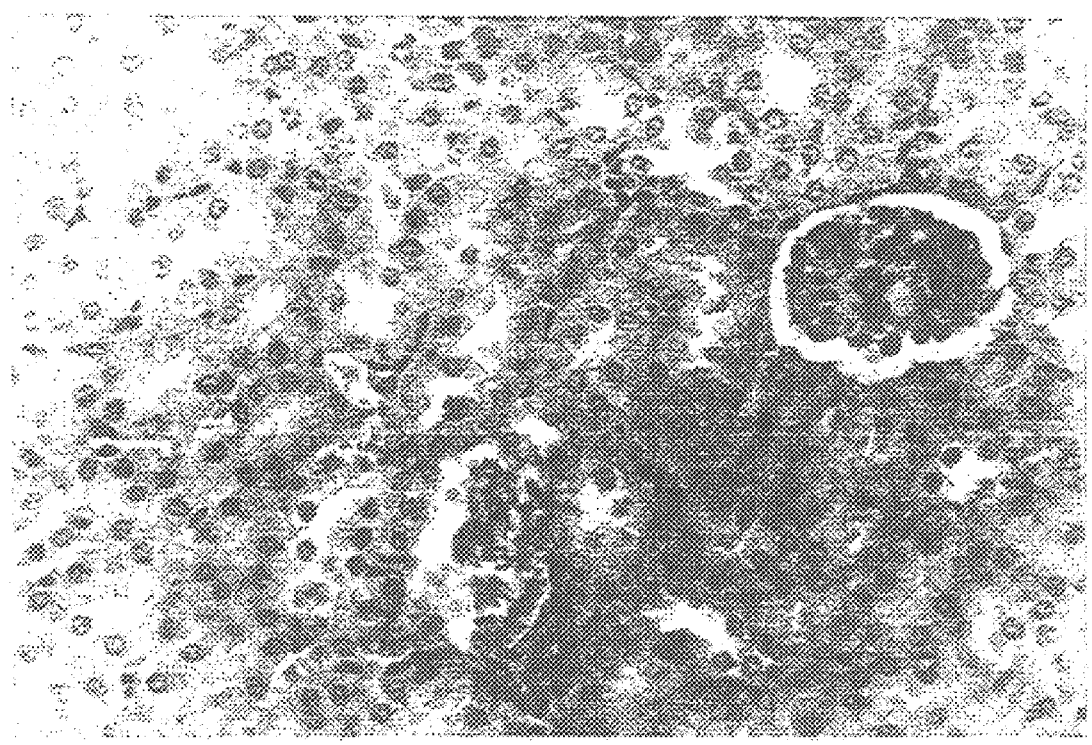
FIG. 7C—kidneys of mice receiving AG1714 prior to cisplatin administration showing normal kidney structure.
Figure 7D:
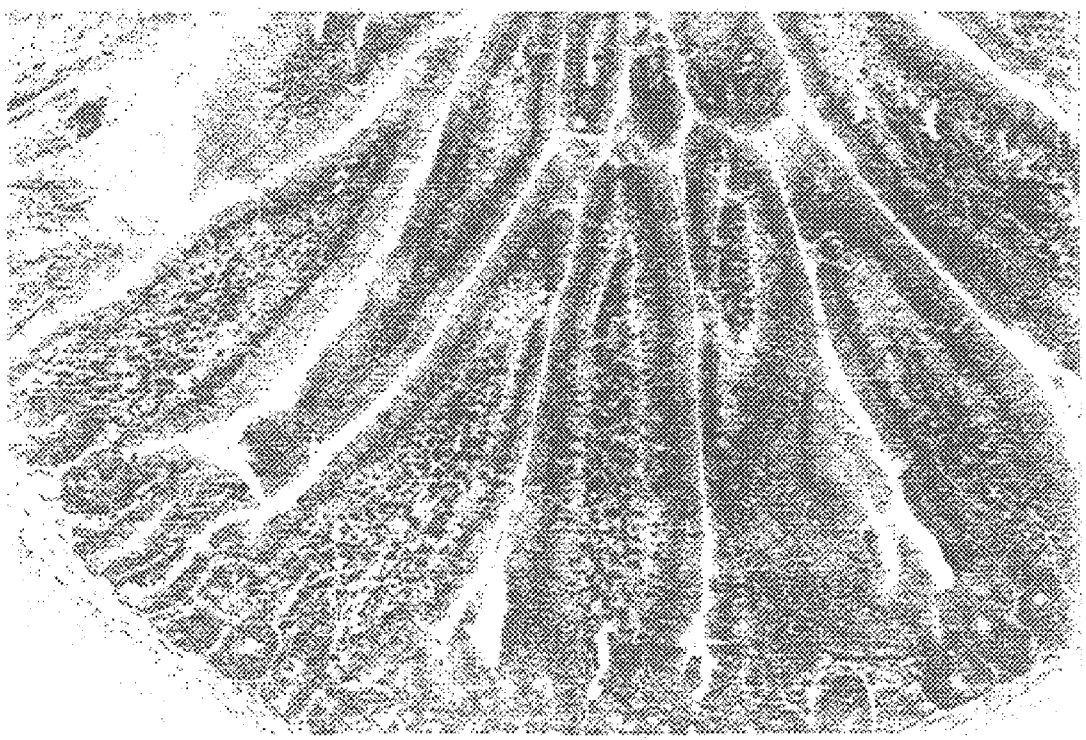
FIG. 7D—small intestines of non-treated mice.
Figure 7E:
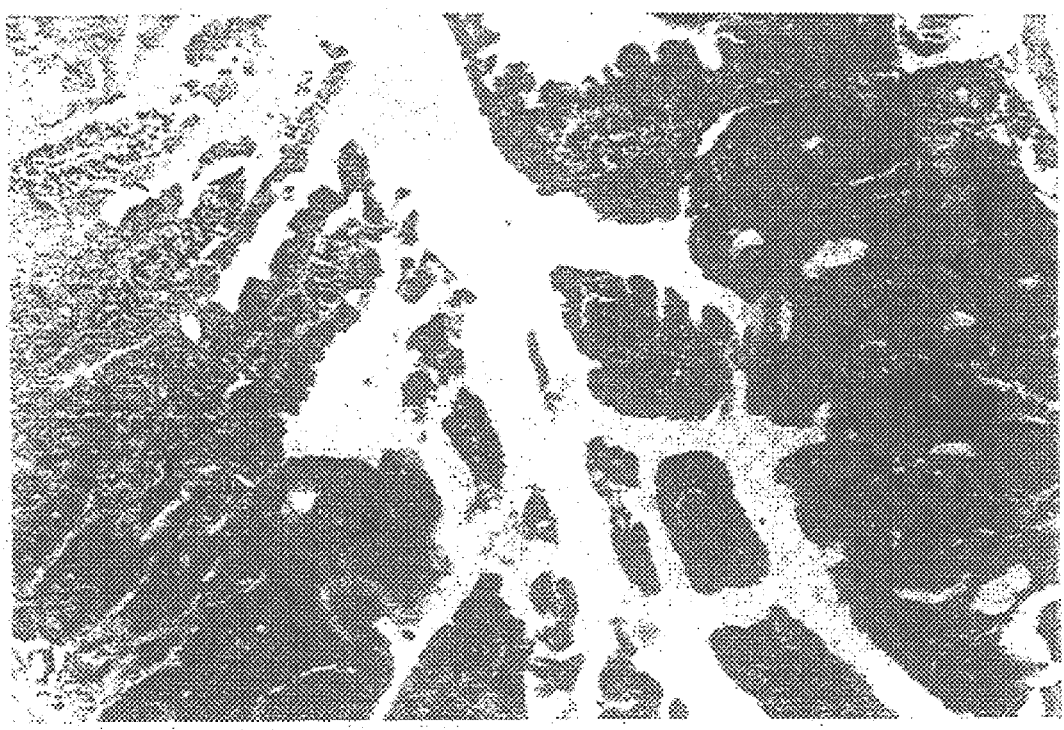
FIG. 7E—small intestine of mice receiving cisplatin alone showing severe necrosis and damage.
Figure 7F:
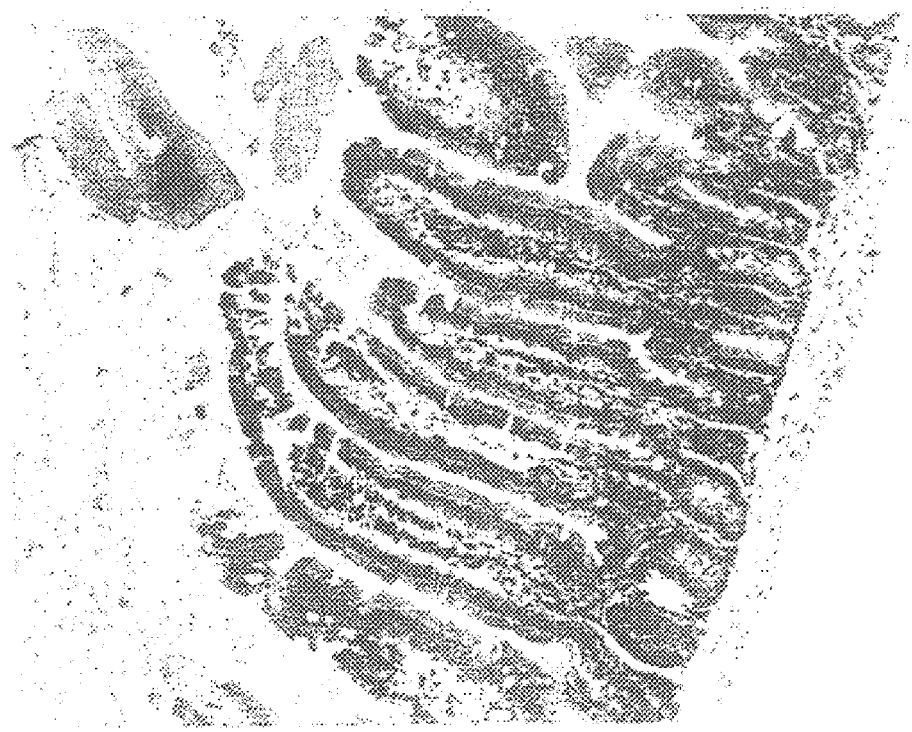

As seen in FIG. 6, administration of cisplatin alone to the mice resulted in elevated levels of creatinine (FIG. 6A) and BUN (FIG. 6B). Table 2 below shows that the levels of ALT and AST were also elevated in these mice. These results indicate both nephrotoxicity as well as damage to the liver of the mice as a result of the administration of cisplatin. As seen in FIG. 6 and Table 2, administration of AG1714 two hours before injection of the cisplatin, resulted in a reduced level of all four measured parameters to their normal level as measured in the control mice.

TABLE 2

Prevention of cisplatin - induced kidney and liver injury by AG1714

| Treatment | ALT u/L | AST u/L |
|---|---|---|
| Control (vehicle) | 30 ± 4.7 | 58 ± 1.5 |
| Cisplatin (14 mg/kg) | 73.5 ± 2.1 | 209 ± 16.0 |
| Cisplatin (14 mg/kg) + AG1714 (20 mg/kg) | 36 ± 3.6 | 70 ± 14.0 |

Example 13

CD1 mice were injected with 14 mg/kg of cisplatin or first with a single i.p. injection of the tyrphostin AG1714 and two hours later an injection of 14 mg/kg of cisplatin. Histopathological analysis of the kidneys and small intestines of the non-treated and treated mice was performed using slices from formaline fixed tissues stained with hematoxylin eosin.

As seen in FIG. 7, kidneys of mice receiving cisplatin alone showed large proteinaceous plaques in the proximal tubals (7B) as well as the appearance of granular material in the columnar epithet. Against this, kidneys of the mice receiving AG1714 injection prior to the cisplatin administration (7C) showed no damage and their structure was similar to that of control mice (7A).

As also seen in FIG. 7, the small intestine of mice receiving cisplatin alone (7E) showed severe necrosis and disintegration of the columnar intestinal epithelial cells as compared to the small intestines of mice receiving AG1714 prior to the cisplatin administration (7F) which showed a normal structure similar to that seen in the small intestine of non-treated mice (7D).

Example 14

In order to test the protective effect of AG1714 against doxorubicin-induced cardiotoxicity, 7 day primary rat cardiomyocytes cultures were prepared according to a standard procedure (described in: In vitro Toxicology, Model System and Methods, Eds. C. McQueen, Telford Press New Jersey, 1990, pg. 163, Primary cultures of neonatal rat myocardial cells, and Kessler-Icekson, G., *J. Mol. Cell Cardiol*, 20:649–755, 1988).

The cardiomyocyte cultures were divided into the following, four groups receiving:
i. Vehicle only (control);
ii. AG1714 as a final concentration of 20 µM;
iii. Cells receiving doxorubicin at a concentration of 10 µM; and
iv. Cells receiving AG1714 at a final concentration of 20 µM followed one hour later by the addition of doxorubicin (10 µM).

The rate of beats-of clusters of cardiomyocytes ("mini-hearts") was determined 24 hours after beginning of incubation.

As seen in Table 3, in the cell cultures incubated with doxorubicin alone, the number of beats per minute was significantly reduced to about 20% of that of the control cultures incubated with the vehicle only. Against this, in cultures incubated with doxorubicin together with AG1714, the number of beats per minute was similar to the number of beats per minute in the control cultures. Similar results (not shown) were seen in the above cardiomyocyte cultures 16 hours and 40 hours after incubation. Thus, incubation of the cultures with AG1714 one hour before the addition of doxorubicin prevented the cardiotoxic effect of doxorubicin on the cell cultures.

TABLE 3

Protective effect of AG1714 against Doxorubicin-induced cardiotoxicity, in vitro

| Treatment | Cellular beating (beats/min) |
|---|---|
| Control (vehicle) | 78 ± 2.0 |
| AG1714 (20 µM) | 68 ± 2.2 |
| Doxorubicin (10 µM) | 15 ± 1.3 |
| Doxorubicin + AG1714 | |

Example 15

The FAS antigen is a cell surface protein belonging to the two factor/nerve growth factor receptor family and have been shown to mediate apoptosis (Itoh, N. et al., *Cell*, 66:233-243 (1991)). Intraperitoneal administration of an anti-FAS antibody into mice was shown to cause severe damage of the liver by apoptosis.

In order to test the effect of the tyrphostin AG1801 and AG1714 on the anti-FAS antibody induced hepatotoxicity, Balb/C mice were injected i.p. either with AG1801 (5 mg/kg) or with AG1714 (5 mg/kg) and two hours later with an i.p. injection of an anti-FAS antibody at a dose of 5 µg/mouse. Another group of mice received only an injection of anti-FAS antibody with no prior treatment with the tyrphostins. Five hours after injection of the anti-FAS antibody, the animals were sacrificed and the level of two transaminases AST and ALT in the serum of the sacrificed mice was determined: a high level of these transaminases indicating hepatotoxicity (Ogasaware, J., et al., *Nature*, 364:806–809, 1993).

Figure 8:
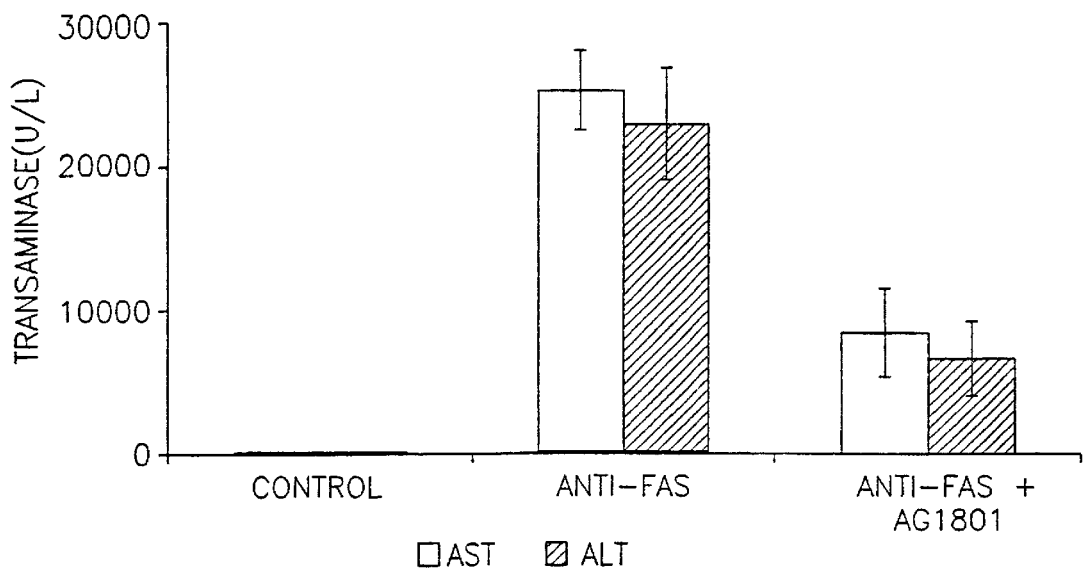
FIG. 8 is a graphic representation showing the level of two transaminases, Aspartic transaminase (AST) and Alanine-transaminase (ALT) in serum of mice receiving an injection of anti-FAS antibody alone or in combination with the tyrphostin AG1801. High levels of the transaminases indicate anti-FAS antibody induced; damage to the liver (hepatotoxicity)
Figure 9:
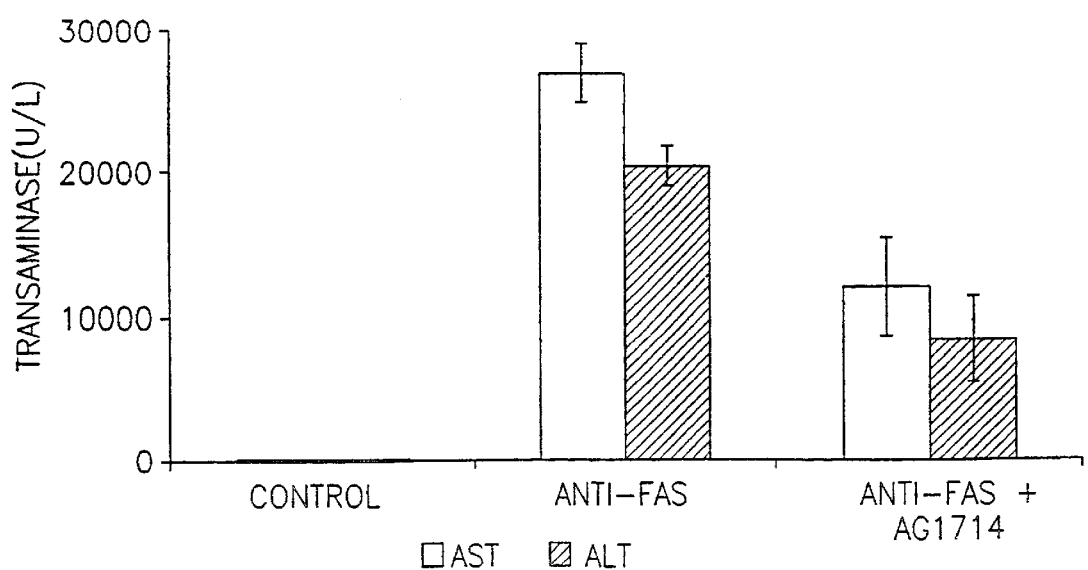
FIG. 9 is a graphic representation showing the level of two transaminases AST and ALT in serum of mice receiving an injection of anti-FAS antibody alone or in combination with the tyrphostin AG1714; High levels of the transaminases indicate anti-FAS antibody induced damage to the liver (hepatotoxicity)

As seen in FIGS. 8 and 9, the level of AST and ALT in the serum of mice treated with the anti-FAS antibody alone was very high indicating FAS antibody induced hepatotoxicity.

Against this, the level of the two transaminases AST and ALT in serum of mice which were treated with AG1801 (FIG. 8) or with AG 1714 (FIG. 9) prior to the anti-FAS injection was significantly lower. Thus, administration of the tyrphostins to mice results in their protection against hepatotoxicity induced by the anti-FAS antibody.

Example 16

T-cell mediated hepatotoxicity is a complication of various disorders and diseases such as Hepatitis B virus infection. Such hepatotoxicity can be induced by injection of Conavalin A (Con A). The effect of AG1714 on Con A induced hepatotoxicity on mice was determined in the following way (see Tiegs, G. et au., *J. Clin. Invest.*, 90:196–203, 1992).

CD1 mice were divided into the following groups:

i. Mice receiving injection of the vehicle only (control);

ii. Mice receiving i.p. injection of AG1714 (10 mg/kg);

iii. Mice receiving an i.v. injection of Con A (35 mg/mouse); and iv. Mice receiving an i.p. injection of AG1714 (10 mg/kg) and two hours later an i.v. injection o(f Con A (35 mg/mouse).

6 hours after injection of Con A to the mice, serum levels of the liver enzymes AST and ALT of the treated mice were determined as explained above. Increase of serum levels of these enzymes reflect liver injury.

As seen in FIG. 10, while administration of AG1714 alone had no effect on the mice, injection of Con A caused significant hepatotoxicity in the mice. Administration of AG1714 prior to Con A administration significantly reduced the Con A induced hepatotoxicity in these mice.

Example 17

It is today known that liver damage may be induced by various immune mechanisms such as cytokines as well as by a variety of other agents known to exert an apoptotic effect (e.g,. alcohol or paracetemol). A model for such liver injury induced by apoptosis was developed in which the hepatic damage is induced in vivo by the injection of galactosamine and TNF-α (see Leist, M., et al., J. Immunol., 153:1778–1788, 1994).

The effect of AG1714 on TNF-induced liver damage in mice was determined as follows.

Mice were divided into the following four groups:

i. Mice receiving an injection of the vehicle alone;

ii. Mice receiving 1 i.p. injection of AG 1714 (10 mg/kg);

iii. Mice receiving, an i.v. injection of human TNF-α (0.25 µg/mouse) in combination with galactosamine (GalN) (18 ml/mouse, i.p.); and iv. Mice receiving the treatment of group iii above together with an injection of AG 1714 (10 mg/kg) injected i.p. two hours prior to TNF/GalN injection. 7 hours after injection of the TNF/GalN, the serum levels of the liver enzymes AST and ALT in the serum of the various treated mice was determined as described above.

Figure 11:
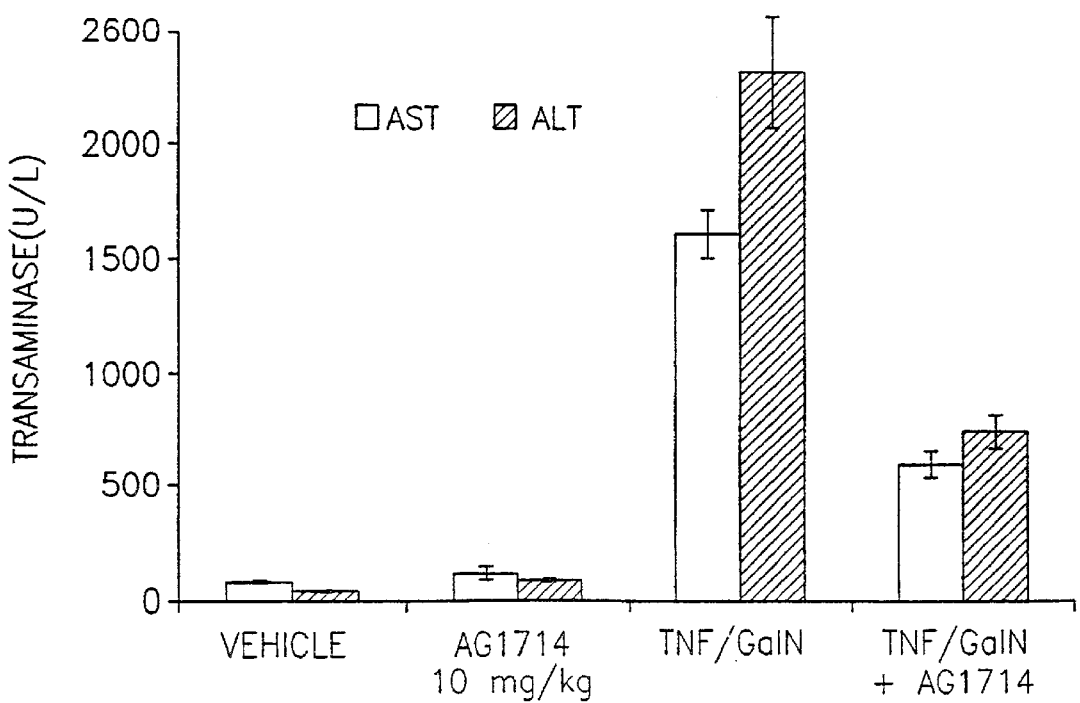
FIG. 11 is a graphic representation showing the level of AST and ALT in serum of mice treated with TNF/GalN or in combination with the tyrphostin AG1714.

As can be seen in FIG. 11, injection of AG1714 prior to the administration of TNF/GalN to the mice significantly reduced the hepatotoxicity induced by the TNF/GalN administration. The tyrphostins may therefore be useful in the reduction of liver damage induced by various immune mechanisms.

III. Reduction of the Toxic Effect of Various Harmful Agents on Nucleated Bone Marrow Cells (Myelotoxicity) and Lymphocytes (Lymphotoxicity) by Tyrphostins Example 18

CD1 mice were divided into the following groups:

i. Mice receiving an i.p. injection of doxorubicin (10 mg/kg) alone;

ii. Mice receiving an i.p. injection of AG1714 (20 mg/kg) and two hours later an i.p. injection of doxorubicin (10 mg/kg); and iii. Mice receiving one injection of the vehicle and two hours later an i.p. injection of doxorubicin (10 mg kg,).

3 days later, the number of bone marrow nucleated cells and colony forming units (CFU) in the femurs of the treated mice was determined (Nikerich, D. A., et al., J. Immunopharmacol., 8:299–313, 1986). Each group contained 3 mice and the results are expressed as a means ±SD.

Figure 12B:
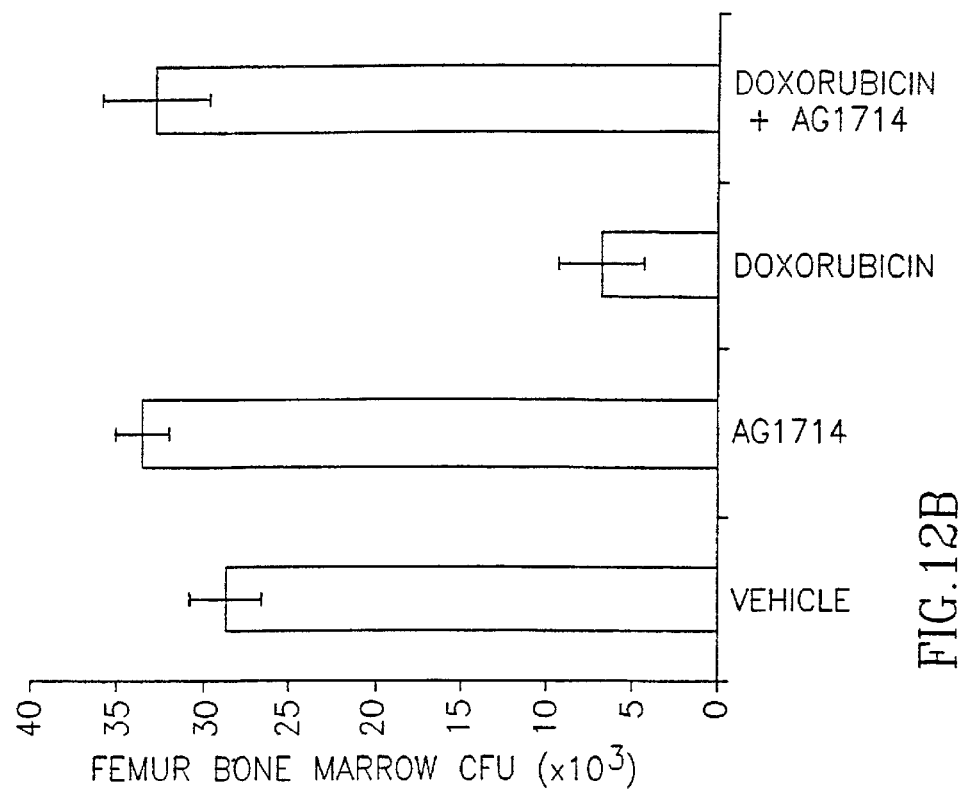
FIG. 12 is a graphic representation showing the number of bone marrow nucleated cells (FIG. 12A) or the number of colony forming units (CFU) (FIG. 12B) in femur bone marrow of mice treated with doxorubicin alone, AG1714 alone or with their combination.
Figure 12A:
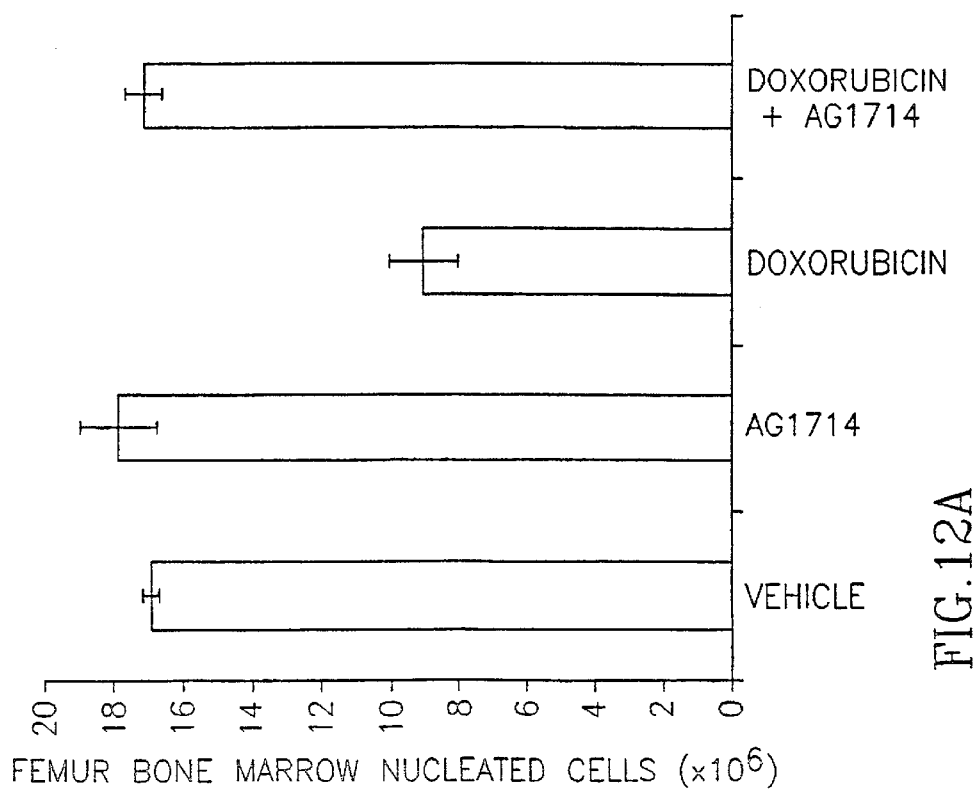

As seen in FIG. 12, injection of doxorubicin to mice resulted 3 days later in myelotoxicity as manifested by 47% reduction in the number of nucleated cells (FIG. 12A) and 55% reduction in CFU (FIG. 12B). Mice who were pretreated with AG 1714 two hours prior to doxorubicin injection were fully protected against its myelotoxicity effects.

Example 19

The effect of AG1714 on myelotoxicity induced by doxorubicini at different doses was investigated. Mice were treated as described in Example 18 above. The number of femur nucleated bone marrow cells in the treated mice was determined three days (FIG. 13A) and at various times (FIG. 13B) post doxorubicini administration.

Figure 13B:
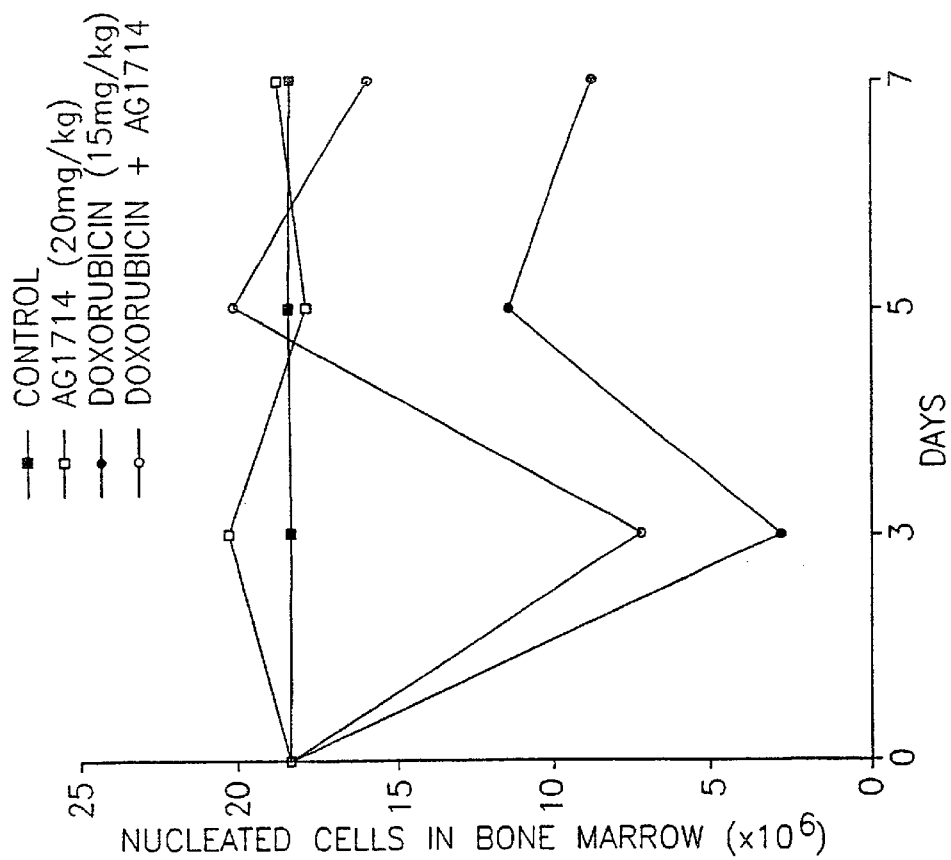
FIG. 13B shows the number of nucleated cells in bone marrow of the treated mice at different periods of time after treatment with doxorubicin.
Figure 13A:
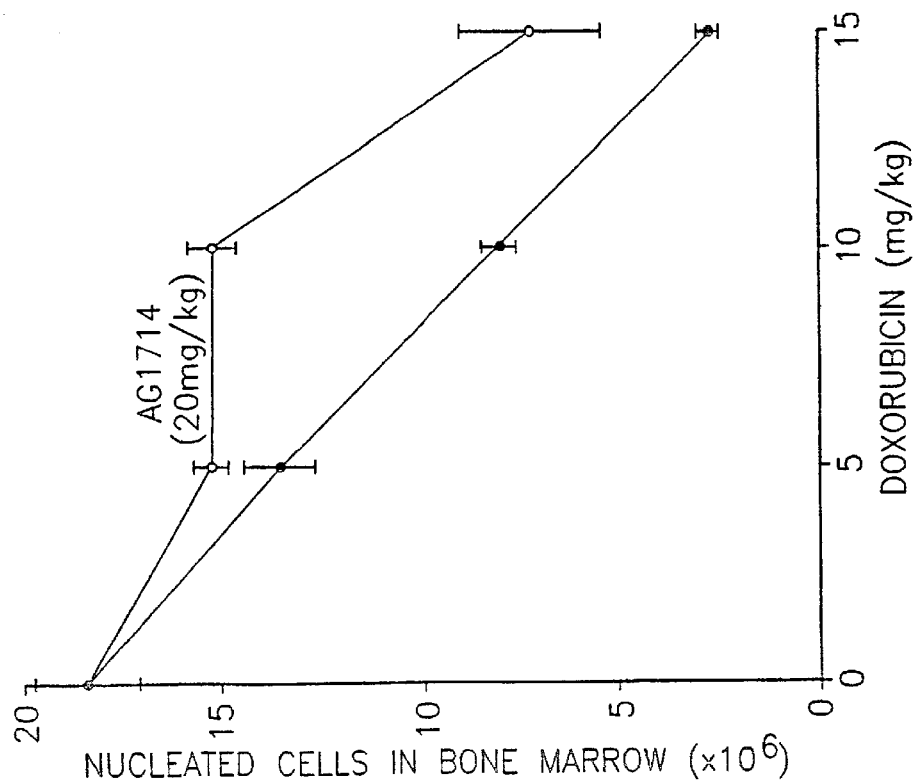
FIG. 13A shows the number of nucleated cells in bone marrow of the mice receiving different doses of doxorubicin.

As seen in FIG. 13A, administration of doxorubicin to mice at a concentration of 10 mg/kg and 15 mg/kg induced myelotoxicity in the treated mice. Pretreatment with AG1714 reduced the doxorubicin induced myelotoxicity significantly.

As seen in FIG. 13B, pretreatment of mice administered with doxorubicin with AG 1714, resulted also in a rapid recovery of bone marrow cells after doxorubicin administration. 5 days after treatment with doxorubicin (15 mg/ks) alone, the number of bone marrow cells in the femurs of the treated mice was still significantly reduced. Pretreatment of the mice with AG1714 prior to the doxorubicin administration, fully reconstituted their bone marrow at that time.

Example 20

CD1 mice received either a single i.p. injection of doxorubicin (10 mg/kg) or first single i.p. injection of AG1714 (20 mg/kg) and two hours later, an i.p. injection of doxorubicin 10 mg/kg). 72 hours after doxorubicin administration the mice were sacrificed and the weight of the spleen and thymus of the mice was determined as parameters of lymphotoxicity. Each experimental group consisted of three mice and the results are mean no. of cells±SD. As control, the mice received an injection of the vehicle only instead of doxorubicin.

Figure 14B:
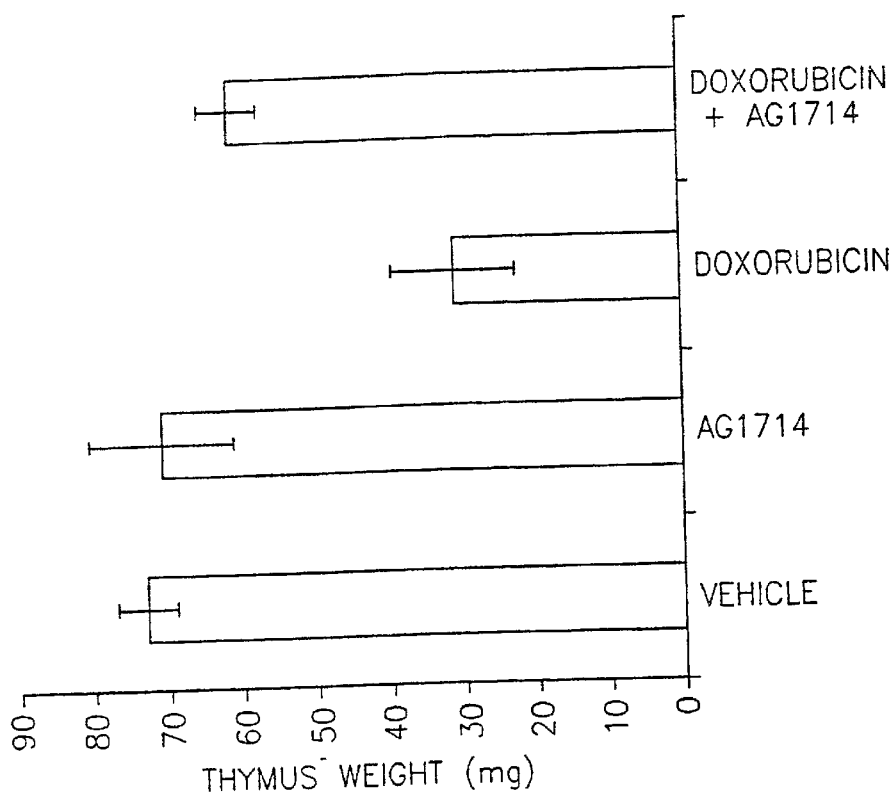
FIG. 14 is a graphic representation showing the weight of the spleen (FIG. 14A) and thymus (FIG. 14B) of mice treated either with doxorubicin alone or with AG1714 prior to doxorubicin administration.
Figure 14A:
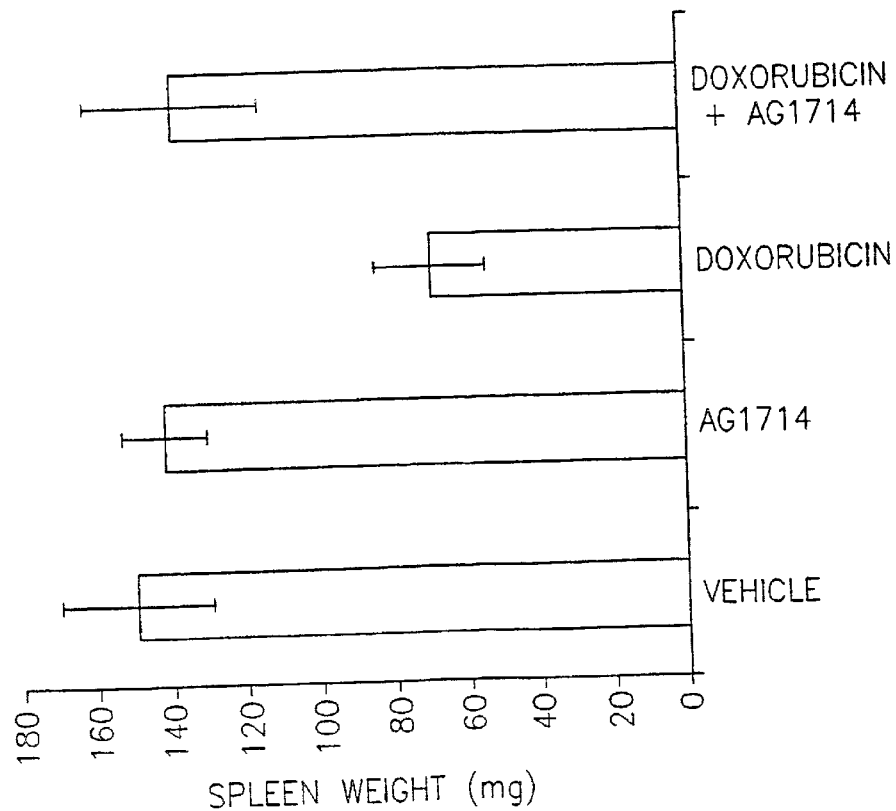

As seen in FIG. 14 below, the administration of doxorubicin alone caused a significant reduction in the weight of spleens (FIG. 14A) and thymuses (FIG. 14B) of the mice. This myelotoxic and lymphotoxic effect of doxorubicin was significantly reduced by the administration of AG1714 to the mice two hours before administration of the doxorubicin.

Example 21

CD1 mice were injected with a single i.p. injection of cyclophosphamide at a dose of 50 mg/kg and divided into the following groups:

i. Mice receiving a single i.p. injection of the vehicle only two hours before administration of the cyclophosphamide;

ii. Mice receiving a single i.p. injection of AG1714 (20 mg/kg) two hours before cyclophosphamide;

iii. Mice receiving a single i.p. injection of AG1801 (2.5 mg/kg) two hours before cyclophosphamide administration. 72 hours after cyclophosphamide administration the mice were sacrificed and the nucleated cells in the bone marrow, spleen and thymus of the mice were counted. Each experimental group consisted of three mice and the results shown are the mean number of cells in a group±SD.

As seen in Table 4A and B, administration of cyclophosphamide caused a significant reduction in the number of nucleated cells in the bone marrow, spleen and thymus indicating myelotoxic and lymphotoxic effect of cyclophosphamide. Administration of the tyrphostins AG1714 or AG1801 prior to the administration of cyclophosphamide, resulted in a reduction in the myelotoxic and lymphotoxic effect of cyclophosphamide in the above three organs. The number of nucleated cells in these organs was higher than in organs of mice receiving cyclophosphamide alone although the level of the nucleated cells in the bone marrow, spleen and thymus of the mice treated with the tyrphostins did not reach control level.

TABLE 4a and b

AG1714 and AG1801 prevent Cyclophosphamide-induced myelotoxicity and lympholysis AG1714 (20 mg/kg)

| Treatment | Nucleated cells in bone marrow ($\times 10^6$) | | Spleen (mg) | | Thymus (mg) | |
|---|---|---|---|---|---|---|
| | − | + | − | + | − | + |
| Vehicle | 17.3 ± 1.33 | 17.9 ± 1.1 | 109 ± 20.0 | 112 ± 11.3 | 75 ± 4.0 | 71 ± 9.8 |
| Cyclophosphamide (50 mg/kg) | 6.2 ± 0.31 | 11.2 ± 0.6 | 52 ± 2.5 | 87 ± 2.0 | 39 ± 6.1 | 57 ± 3.6 |

AG 1801 (2.5 mg/kg)

| Treatment | Nucleated cells in bone marrow ($\times 10^6$) | | Spleen (mg) | | Thymus (mg) | |
|---|---|---|---|---|---|---|
| | − | + | − | + | − | + |
| Vehicle | 17.3 ± 1.33 | 18.6 ± 1.0 | 109 ± 20.0 | 97 ± 1.52 | 75 ± 4.0 | 74 ± 7.9 |
| Cyclophosphamide (50 mg/kg) | 6.2 ± 0.31 | 10.9 ± 0.9 | 52 ± 2.5 | 69 ± 0.58 | 39 ± 6.1 | 57 ± 5.6 |

Example 22

CD1 female mice were divided into the following groups:
i. A control group receiving a single i.p. injection of the vehicle only (co-solvent: propylene carbonate-cremophor-saline);
ii. Mice receiving a single i.p. injection of 5-fluorouracil (5 FU) at a dose of 80 mg/kg;
iii. Mice receiving a single i.p. injection of AG1714 at a dose of 20 mg/kg;
iv. Mice receiving a single i.p. injection of AG1801 at a dose of 2.5 mg/k;
v. Mice receiving, a single i.p. injection of AG1843 at a dose of 5 mg/kg;
vi. Mice receiving a single i.p. injection of AG1714 (20 mg/kg) and two hours later a single i.p. injection of 5 FU (80 mg/kg);
vii. Mice receiving a single i.p. injection of AG1801 (2.5 mg/kg) and two hours later a single i.p. injection of 5 FU (80 mg/kg); and
viii. Mice receiving a single i.p. injection of AG1843 (5 mg/kg) and two hours later a single i.p. injection of 5 FU (80 mg/kg).

Five days after the administration of 5 FU to the mice, the mice were sacrificed and the number of nucleated cells in the bone marrow of one femur, were counted. Each group of mice consisted of two or three mice and the results shown are the mean number of cells counted±SD.

Figure 15:
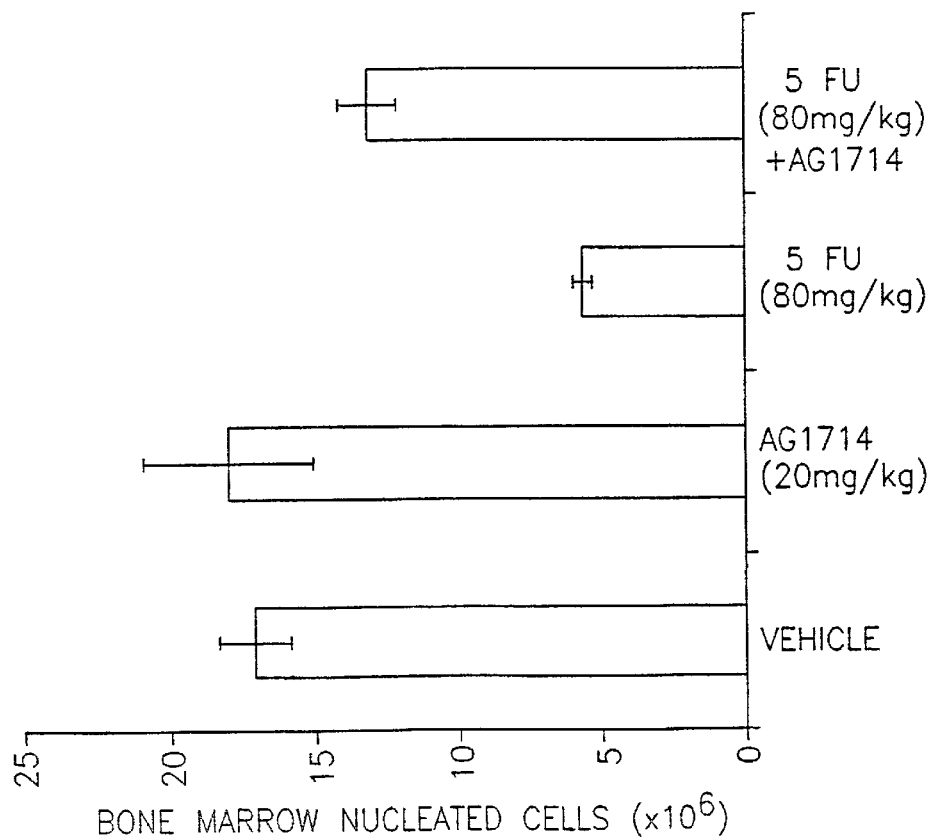
FIG. 15 is a graphic representation showing the number of bone marrow nucleated cells in the femurs of mice treated with 5FU alone or with 5FU and AG1714.

As seen in FIG. 15, administration of 5 FU to the mice resulted in a decrease in the number of nucleated cells in the bone marrow of these mice. The administration of the AG1714 before 5 FU administration to the mice, resulted in a significantly lower reduction in the number of cells in the bone marrow. Thus the AG1714 reduced the myelotoxic effect of 5 FU in these mice.

Example 23

CD1 female mice were divided into the following groups:
i. A control group receiving a single i.p. injection of the vehicle only (co-solvent: propylene carbonate-cremophor-saline);
ii. Mice receiving a single i.p. injection of mitomycin-C at a dose of 2 mg/kg;
iii. Mice receiving a single i.p. injection of AG1714 at a dose of 20 mg/kg;
iv. Mice receiving a single i.p. injection of AG1714 (20 mg/kz,) and two hours, later a single i.p. injection of mitomycin-C (2 mg/kg);

As described in Example 22 above, five days after the administration of mitomycin-C to the mice, the mice were sacrificed and the number of nucleated cells in the bone marrow of one femur, were counted. Each group of mice consisted of two or three mice and the results shown are the mean number of cells courted±SD.

Figure 16:
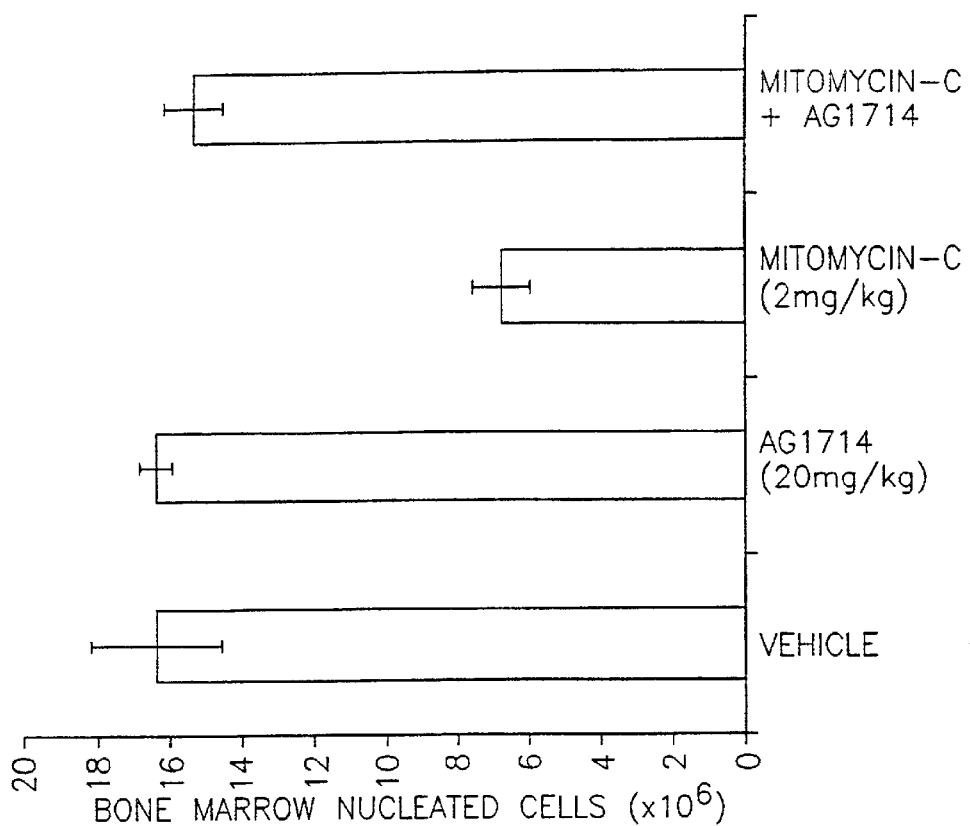
FIG. 16 is a graphic representation showing the number of bone marrow nucleated cells in the femurs of mice treated with mitomycin-C alone or with mitomycin-C and AG1714.

As seen in FIG. 16, mice receiving mitomycin-C alone showed a very low count of nucleated cells in their bone marrow. While administration of AG1714 alone had no effect on the mice, its administration prior to the administration of mitomycin-C to the mice resulted in a reduction in the myelotoxic effect of the mitomycin-C in these mice and provided almost full protection from the harmful effects of the mitomycin-C bringing the nucleated cell count in the bone marrow of these mice to the level of control mice receiving the cosolvent only.

Example 24

The effect of various doses of AG1801 against doxorubicin induced myelotoxicity in mice was determined. CD1 mice were divided into five groups:
i. Mice receiving the vehicle alone;
ii. Mice receiving doxorubicin (10 mg/kg) alone;
iii. Mice receiving an i.p. injection of AG1801 (0.5 mg/kg) two hours prior to doxorubicin administration;
iv. Mice receiving an i.p. injection of AG1801 (1 mg/kg) two hours prior to doxorubicin administration; and
v. Mice receiving an i.p. injection of AG1801 (2 mg/kg) two hours prior to doxorubicin administration.

Three days after doxorubicin administration, the mice were sacrificed and the number of nucleated cells in bone marrow was determined as described above.

Figure 17:
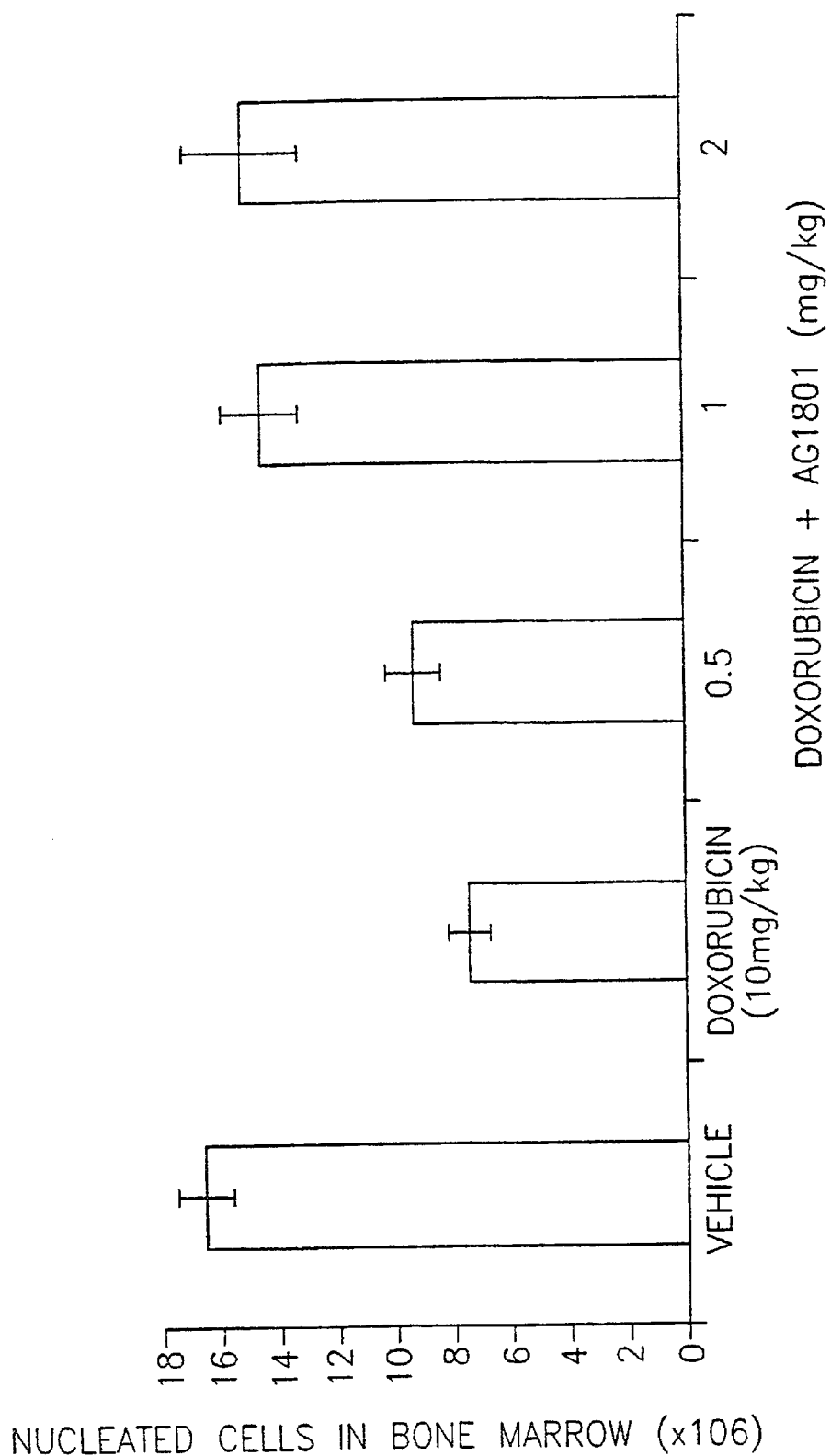
FIG. 17 is a graphic representation showing the number of nucleated cells in bone marrow of mice treated with doxorubicin alone or with AG1801 at different doses prior to doxorubicin administration.

As seen in FIG. 17, administration of AG1801 to the mice had a protective effect against doxorubicin induced myelotoxicity which was dose dependent.

IV Reduction of Radiation-induced Toxicity by Tyrphostins

Example 25

In order to test the protective activity of the tyrphostin AG1714 in radiated mice, CD1 mice irradiated with a radiation dose of 300R using a cobalt source were divided into two groups:

i. Mice receiving no further treatment; and ii. Mice receiving a single i.p. injection of the tyrphostin AG1714 at a dose of 20 mg/kg two hours before irradiation.

A third group of mice received only a single injection of AG1714 (20 mg/kg) and a fourth group of mice served as control mice which were not treated.

At different periods of time after irradiation, mice were sacrificed and the number of cells in the bone marrow of one femur were counted.

Figure 18:
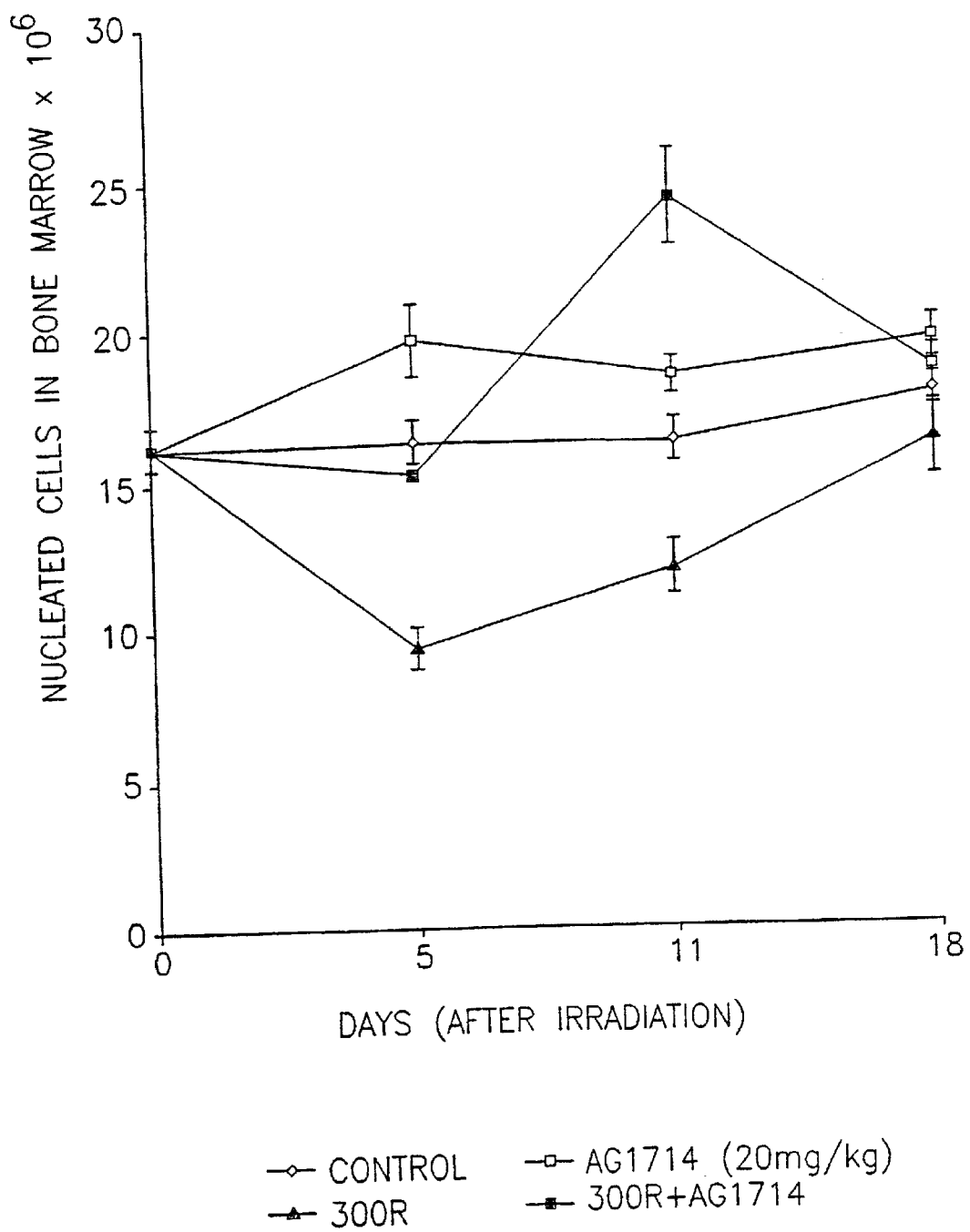
FIG. 18 is a graphic representation showing the number of nucleated cells in bone marrow of irradiated mice (300R) and of mice treated with the tryphostin AG1714 before irradiation.

As seen in FIG. 18, irradiation of the mice with 300R caused a decrease in the number of cells in the bone marrow of these mice as compared to untreated mice or mice treated only with AG1714. Reconstitution of cells in the bone marrow of the irradiated mice began about five days after their radiation. Treatment of the irradiated mice with AG1714 prevented the decrease in the number of cells in the bone marrow of the irradiated mice and caused a very significant enhancement of the number of cells in their bone marrow. Thus, the tyrphostin AG1714 has a protective effect against myelotoxicity caused by irradiation.

Example 26

The protective effect of the tyrphostin AG 1714 against myelotoxicity caused by a high dose irradiation (450R) was tested as described in Example 25 above except that the dose of irradiation was 450R instead of 300R.

Figure 19:
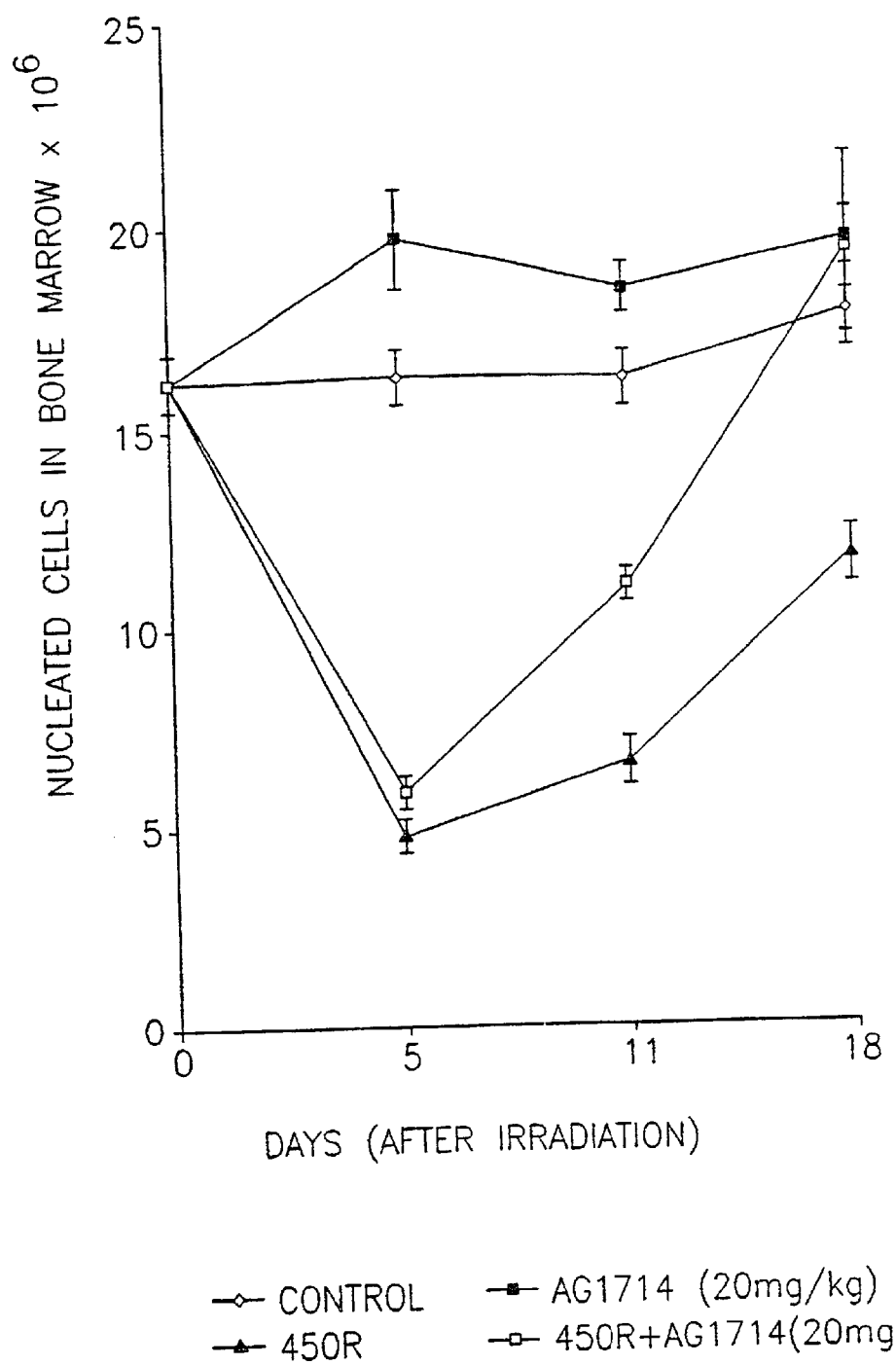
FIG. 19 is a graphic representation showing the number of cells in bone marrow of irradiated mice (450R) and of mice treated with tyrphostin AG1714 before irradiation.

As seen in FIG. 19, the number of cells in the bone marrow of mice irradiated with 450R was significantly reduced five days after radiation indicating a severe myelotoxic effect of the irradiation on these mice. Five days after irradiation reconstitution of the number of cells in the bone marrow began but 18 days after radiation, the number of cells in the bone marrow of the irradiated mice still remained significantly lower than the number of cells in the bone marrow of non-treated mice or mice receiving AG1714 alone. In the bone marrow of mice receiving AG1714 has a 1714 before their irradiation, myelotoxic effect was also seen until five days after radiation. However, after five days, a significant reconstitution was seen in the number of cells in the bone marrow of these mice and 18 days after irradiation, the number of cells in the bone marrow of the irradiated mice receiving AG1714 was higher than the number of cells in the control mice. Administration of AG1714 thus enhance the reconstitution of the number of cells in the bone marrow of mice irradiated by high. dose irradiation.

Example 27

CD1 mice were irradiated with a lethal 800R dose using a cobalt source, and divided into two groups:

i. Mice receiving irradiation only; and ii. Mice receiving a single i.p. injection of AG1714 at a dose of 20 mg/kg, one hour before irradiation.

Each group of mice consisted of 10 mice and the % mortality in each group was tested by scoring the number of dead mice each day after irradiation.

Figure 20:
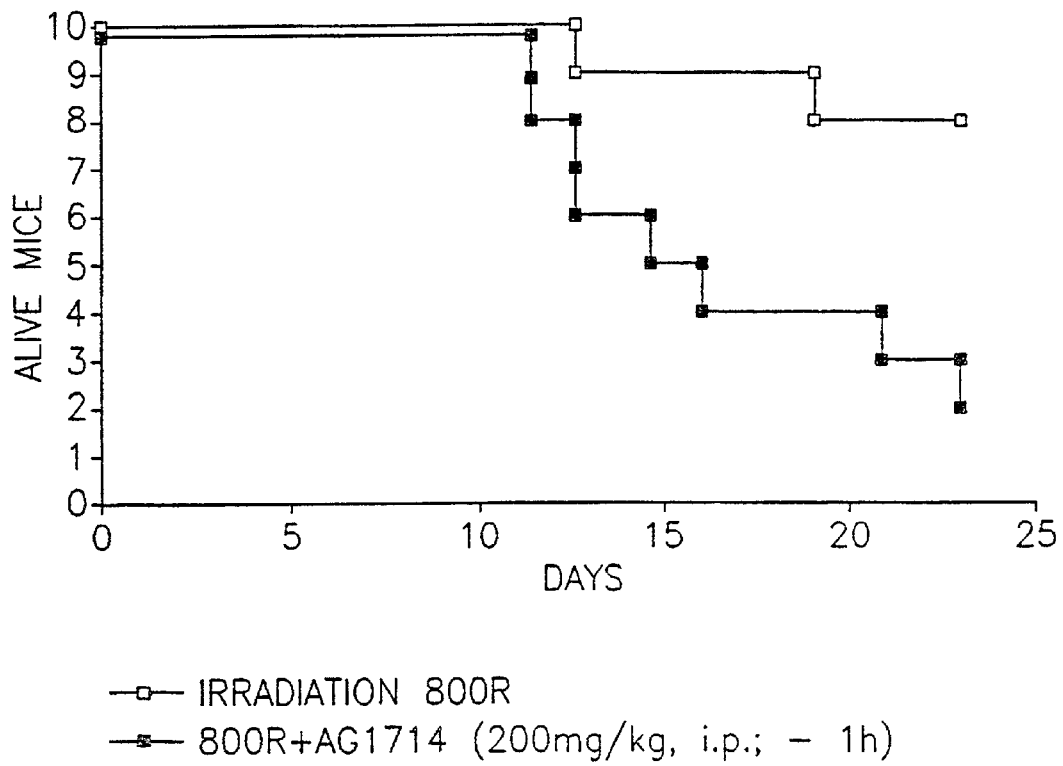
FIG. 20 is a graphic representation showing the mortality of mice after lethal irradiation (800R) as compared to the mortality of mice treated with tyrphostin AG1714 prior to irradiation over a period of 23 days after irradiation.

As seen in FIG. 20, in the group of mice receiving an 800R irradiation, mortality of the mice began 10 days after irradiation and the % mortality in this group reached the rate of 80% 23 days after their irradiation. Against this, the % mortality in the group of mice receiving AG1714 before their irradiation was significantly reduced to 20% mortality 20 days after irradiation.

The mortality in both groups did not change further until 50 days after irradiation.

V. The Effect of Tyrphostins on Anti-tumor Activity of Chemotherapeutic Agents

Example 28

The effect of AG1714 on the anti-tumor effect of chemotherapy was determined using a variety of experimental tumor models in mice.

$2 \times 10^5$/mouse MCA-105 fibrosarcoma cells or Lewis Lung carcinoma cells and $5 \times 10^4$/mouse B-16 melanoma cells were injected into the tail vein of C57BL mice.

Cisplatin (4 mg/kg) was injected i.p. 4 days after tumor inoculation. AG1714 (20 mg/kg) or vehicle was injected i.p. 2 hours prior to cisplatin. Twenty-four days after tumor inoculation, mice were sacrificed, lungs weighed and the number of metastases were scored. Each group contained 5 mice and the results are expressed as the means lungs' weights±SE.

Figure 21A:
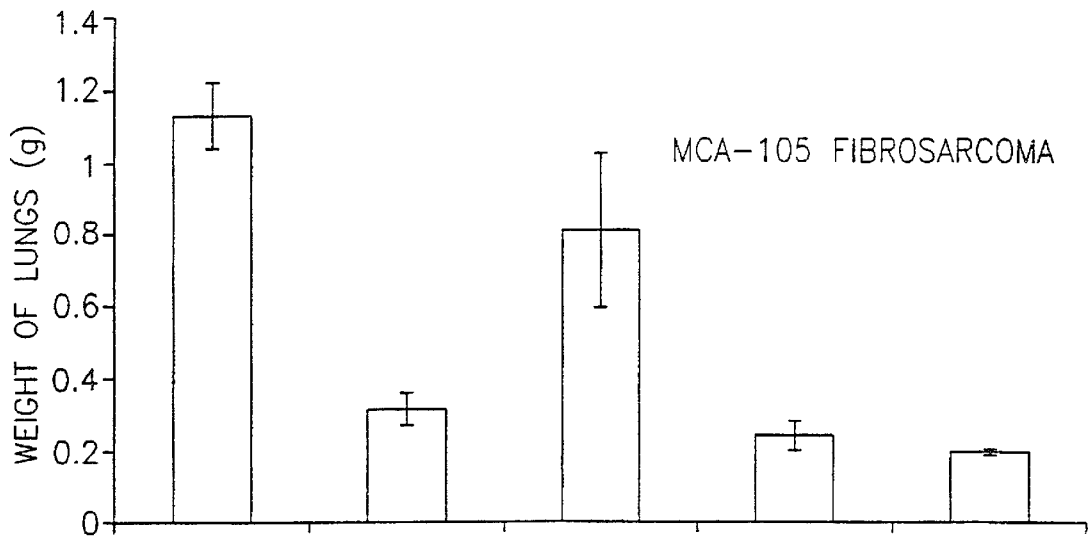
FIG. 21 is a graphic representation showing the weight of lungs of mice inoculated with MCA-105 fibrosarcoma cells (FIG. 21A), Lewis lung carcinoma cells (FIG. 21B) or B-16 melanoma cells (FIG. 21C) and treated with either cisplatin alone, AG1714 alone or with a combination of cisplatin and AG 1714.
Figure 21B:
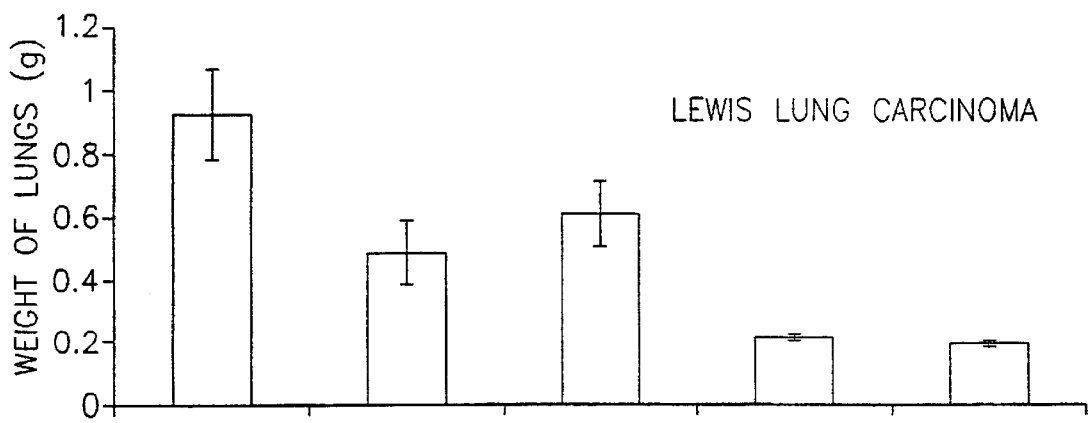

As seen in FIG. 21A, cisplatin markedly inhibited the growth of MCA-105 fibrosarcoma. AG1714 by itself had a small anti-tumor effect. Combined treatment with AG1714 and cisplatin was as effective as cisplatin alone, in suppression of the growth of the established lung metastases of MCA-105. Cisplatin and AG1714 by themselves had a partial anti-tumor effect against Lewis lung carcinoma. Combined treatment with AG1714 and cisplatin was more effective than cisplatin also in suppression of the growth of established lung metastases of this tumor (FIG. 21B).

Figure 21C:
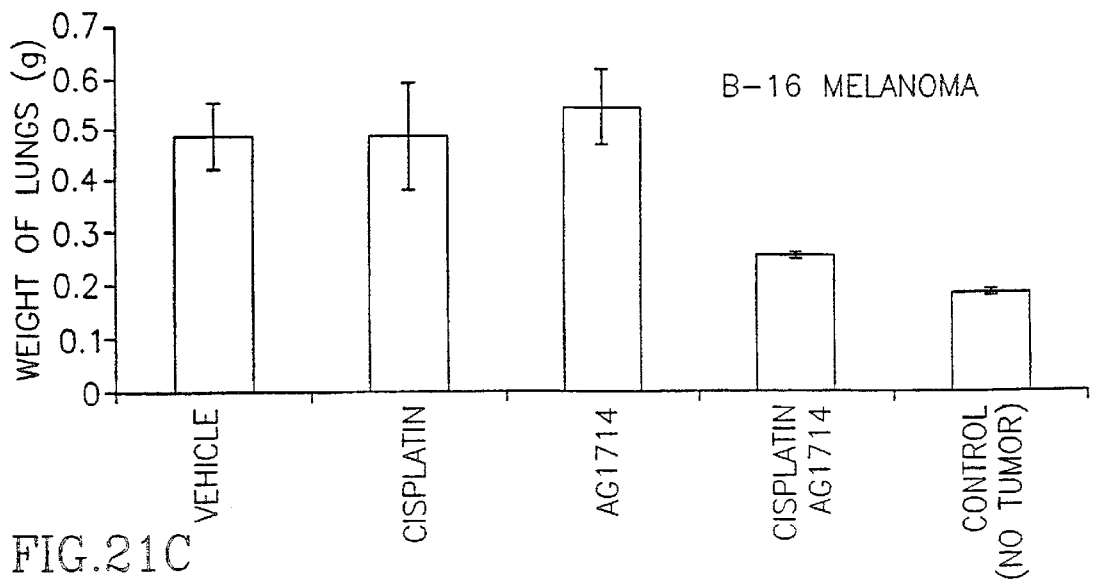

Cisplatin (4 mg/kg) or AG1714 (20 mg/kg) alone were not effective against established lung metastases of B-16 melanoma (FIG. 21C). Combined treatment with these agents was more effective than treatment with each agent alone.

Example 29

The effect of doxorubicin and AG1714 on SK-28 human melanoma tumor xenografts in nude mice was determined as follows:

CD1 athymic mice (nu/nu) were inoculated i.v. with $4 \times 10^5$/mouse SK-28 human melanoma. Doxorubicin (4 mg/kg) was injected i.p. 4 days after tumor inoculation. AG1714 (20 mg/kg or vehicle were injected 2 hours prior to doxorubicin. The weights of the treated mice lungs and number of metastases in the lungs were determined 24 days after tumor inoculation. Each group contained 5 mice and the results are expressed as means±SE.

Figure 22:
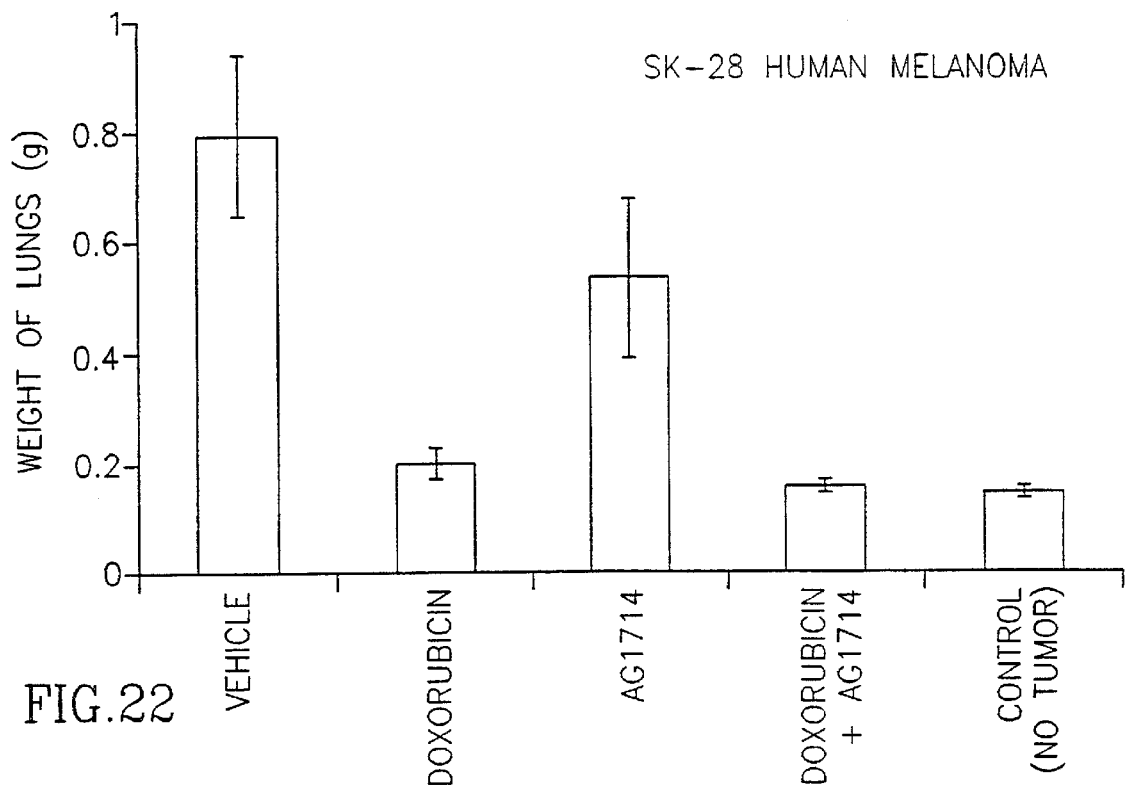
FIG. 22 is a graphic representation showing the weight of nude mice bearing the SK-28 human melanoma tumors and treated with doxorubicin, AG1714 or their combination.

As seen in FIG. 22, doxorubicin markedly suppressed the growth of the SK-28 tumor whereas AG1714 by itself had a small anti-tumor effect. Pretreatment with AG1714 did not impair the effect of doxorubicin alone in the suppression of the growth of this tumor.

Example 30

Athymic mice were inoculated subcutaneously (s.c.) with human ovary carcinoma (OVCAR-3) cells ($3 \times 10^6$ cells/site). Cisplatin (4 mg/kg) was injected 4 days after tumor inoculation. AG1714 (20 mg/kg) or vehicle was injected i.p. 2 hours prior to cisplatin. Twenty days post tumor inoculation the short (S) and long (L) diameters of the tumor were measured and the tumor volume (V) was calculated according to the formula:

$$V=[S^2 \times L]/2.$$

Each group contained 5 mice and the results are expressed as the means±SE.

Figure 23:
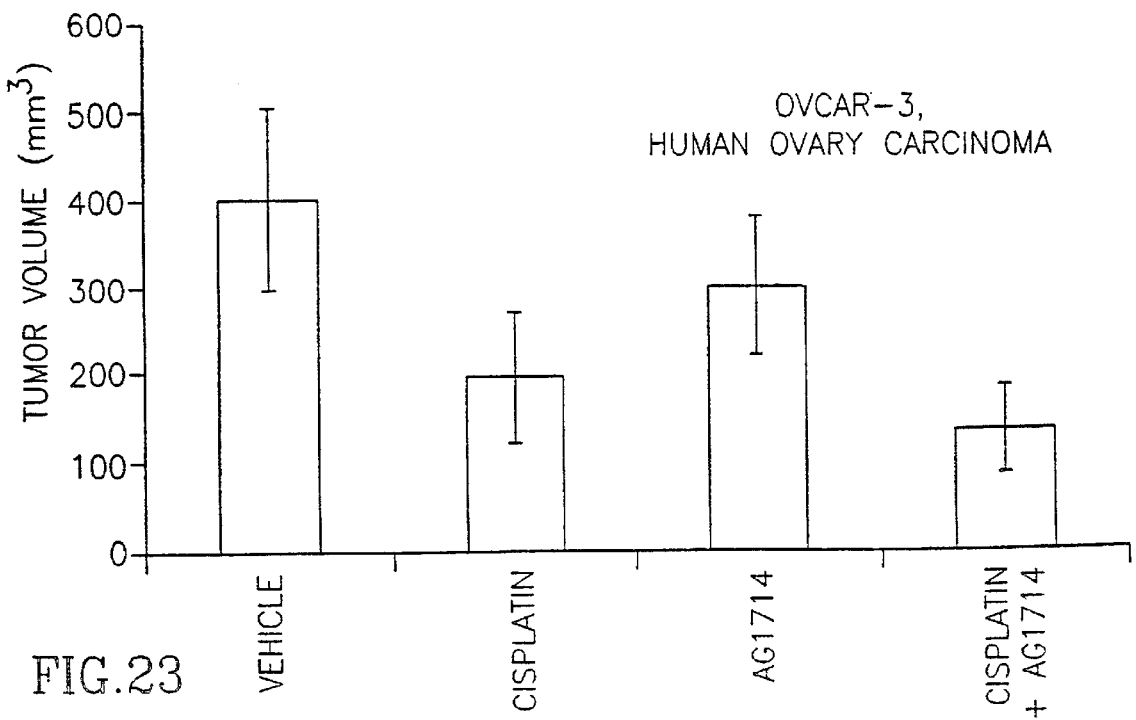
FIG. 23 is a graphic representation showing the volume of the human ovary carcinoma tumor (OVCAR-3) in mice treated either with cisplatin alone, with AG1714 alone or with their combination.

As seen in FIG. 23, cisplatin had a marked anti-tumor effect in the mouse bearing OVCAR-3 tumors whereas AG1714 itself was less effective. Administration of AG1714 did not impair the chemotherapeutic effect of cisplatin.

Figure 24:
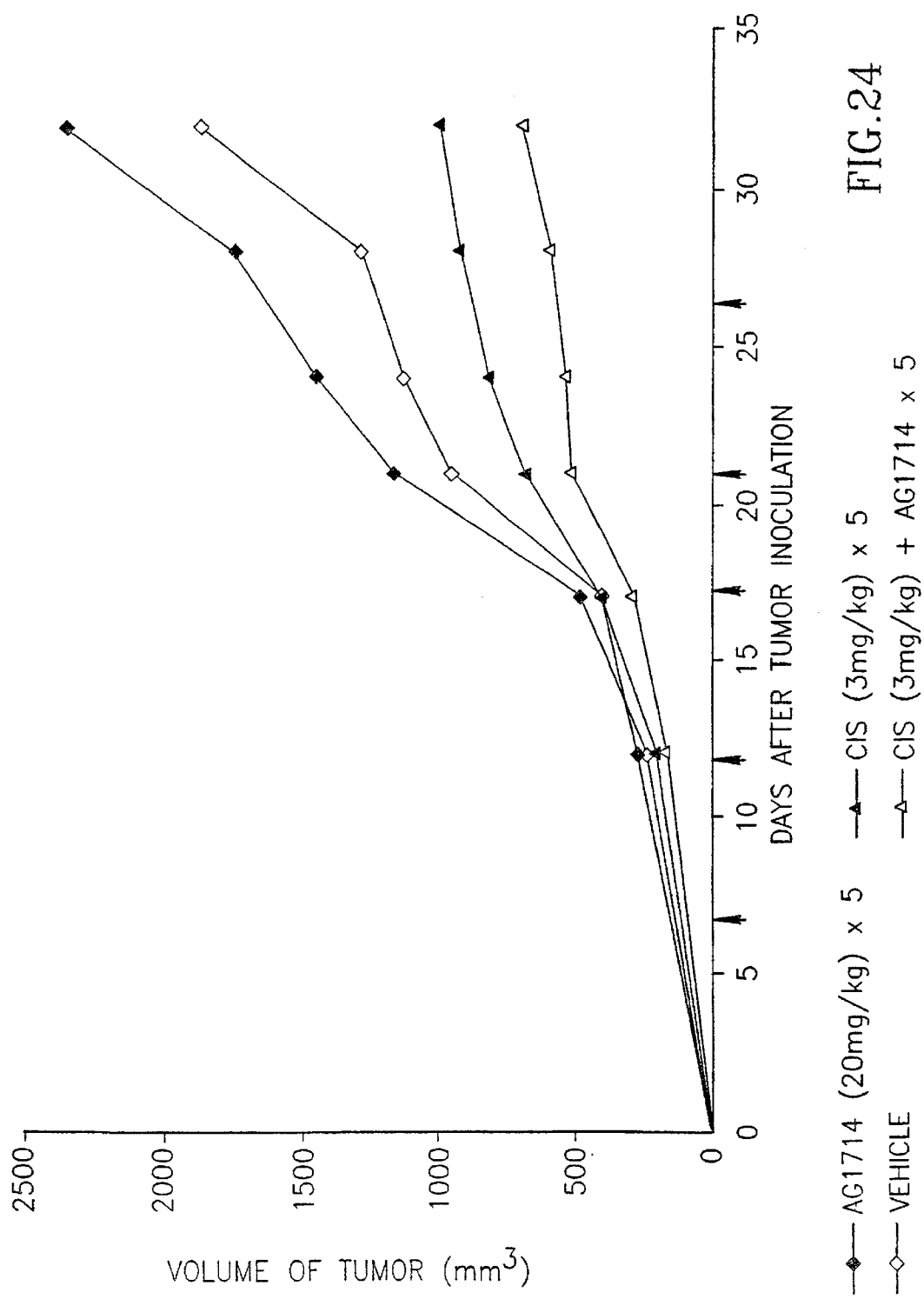
FIG. 24 is a graphic representation showing the volume of the OVCAR-3 tumor in mice receiving repetitive administration of the treatments described in FIG. 23 above.

As seen in FIG. 24, the difference in the diameter of the tumor volume of tumors in mice receiving repeated injections of cisplatin and AG1714 as compared to the volume of tumors in mice receiving repeated injections of cisplatin alone or repeated injections of AG1714 alone.

Example 31

The effect of AG1714 on high dose doxorubicin efficacy was measured by determining the mortality of B-16 melanoma bearing mice and the number of metastases in their lungs or the lung weight.

Mice were injected i.v. with $2 \times 10^5$ B-16 melanoma cells and 4 days after tumor inoculation each mouse received a single i.p. injection of doxorubicin (4 mg/kg or 8 mg/kg). Two hours prior to the doxorubicin injection, each mouse was injected i.p. with AG1714 at a dose of 20 mg/kg.

As seen in Table 5A and B showing two experiments carried out as explained above, administration of low dose doxorubicin resulted in low mortality of the mice and in a significant therapeutic effect. High dose administration of doxorubicin resulted in a much more significant therapeutic effect but resulted in a high mortality rate of the treated mice. AG1714 administered alone showed some therapeutic effect in itself. The combined administration of doxorubicin at a high dose together with AG1714 resulted in the high therapeutic effect of the high doxorubicin, however, the mortality of the mice were significantly reduced.

TABLE 5

Effect of AG1714 on high dose doxorubicin efficacy and mortality in B-16 melanoma bearing mice

A.

| Treatment | No. of lungs' metastases (+ SD) | Mortality (dead/total) |
| --- | --- | --- |
| Vehicle | 29 ± 9 | 0/4 |
| AG1714 (20 mg/kg) | 16 ± 5 | 0/4 |
| Doxorubicin (4 mg/kg) | 7 ± 4 | 0/4 |
| Doxorubicin (4 mg/kg) + AG1714 (20 mg/kg) | 7 ± 6 | 0/4 |
| Doxorubicin (8 mg/kg) | 1 | 3/4 (75%) |
| Doxorubicin (8 mg/kg) + AG1714 (20 mg/kg) | 2 ± 1 | 0/4 |
| No tumor | — | 0/4 |

B.

| Treatment | Lungs' weight (mg + SEM) | Mortality (dead/total) |
| --- | --- | --- |
| Vehicle | 976 ± 142 | 0/6 |
| AG1714 (20 mg/kg) | 870 ± 178 | 0/6 |
| Doxorubicin (4 mg/kg) | 306 ± 12 | 0/6 |
| Doxorubicin (4 mg/kg) + AG1714 (20 mg/kg) | 303 ± 28 | 0/6 |
| Doxorubicin (8 mg/kg) | — | 7/8 (88%) |
| Doxorubicin (8 mg/kg) + AG1714 (20 mg/kg) | 246 ± 10 | 2/8 (25%) |
| No tumor | 232 ± 12 | 0/3 |

Thus the combined administration of AG1714 together with doxorubicin resulted in the intensification of the chemotherapeutic effect of doxorubicin. The significant therapeutic effect of the high dose doxorubicin administered with AG1714 could be achieved while the high mortality rate of the high dose doxorubicin was neutralized by the combined administration.

Such an intensification effect could also be seen in mice bearing, MCA-105 fibrosarcoma tumors and treated with either doxorubicin alone (Table 6A) or cisplatin alone (Table 6B) or with a combination of each of the above with AG1714.

TABLE 6

Effect of AG1714 on high dose doxorubicin efficacy and mortality in MCA-105 fibrosarcoma bearing mice

A.

| Treatment | Lungs' weight (mg + SEM) | Mortality (dead/total) |
| --- | --- | --- |
| Vehicle | 908 ± 107 | 0/8 |
| AG1714 (20 mg/kg) | 632 ± 74 | 0/6 |
| Doxorubicin (4 mg/kg) | 47 ± 119 | 0/5 |
| Doxorubicin (4 mg/kg) + AG1714 (20 mg/kg) | 494 ± 137 | 0/5 |
| Doxorubicin (8 mg/kg) | 170 ± 4 | 5/8 (62.5%) |
| Doxorubicin (8 mg/kg) + AG1714 (20 mg/kg) | 172 ± 6 | 218 (25%) |
| No tumor | 161 ± 12 | 0/4 |

Example 32

The effect of AG1801 on the anti-metastatic activity of cisplatin on established lung metastases of MCA-105 fibrosarcoma bearing mice was determined as follows:

C57BL mice were divided into the following groups:
 i. Mice injected i.v. at the age of 6 weeks with $2 \times 10^5$ fibrosarcoma MCA105 cells and 4 days' later, receiving an injection comprising the vehicle only;
 ii. Mice injected i.v. at the age of 6 weeks with $2 \times 10^5$ fibrosarcoma MCA105 cells and 4 days' later, injected with 10 mg/kg of cisplatin;
 iii. Mice injected i.v. at the age of 6 weeks with $2 \times 10^5$ fibrosarcoma MCA105 cells and 4 days' later, injected with 10 mg/kg of doxorubicin;
 iv. Mice injected i.v. at the age of 6 weeks with $2 \times 10^5$ fibrosarcoma MCA105 cells and 4 days' later, injected with 5 mg/kg of AG1801;
 v. Mice injected i.v. at the age of 6 weeks with $2 \times 10^5$ fibrosarcoma MCA-105 cells and 4 days' later, injected with 5 mg/kg of AG1801 and 2 hours' later, with 10 mg/kg of cisplatin;
 vi. Mice injected i.v. at the age of 6 weeks with $2 \times 10^5$ fibrosarcoma MCA-105 cells and 4 days' later, injected with 5 mg/kg of AG1801 and 2 hours' later, with 10 mg/kg of doxorubicin; and
 vii. Non treated C57BL mice.

Figure 25A:
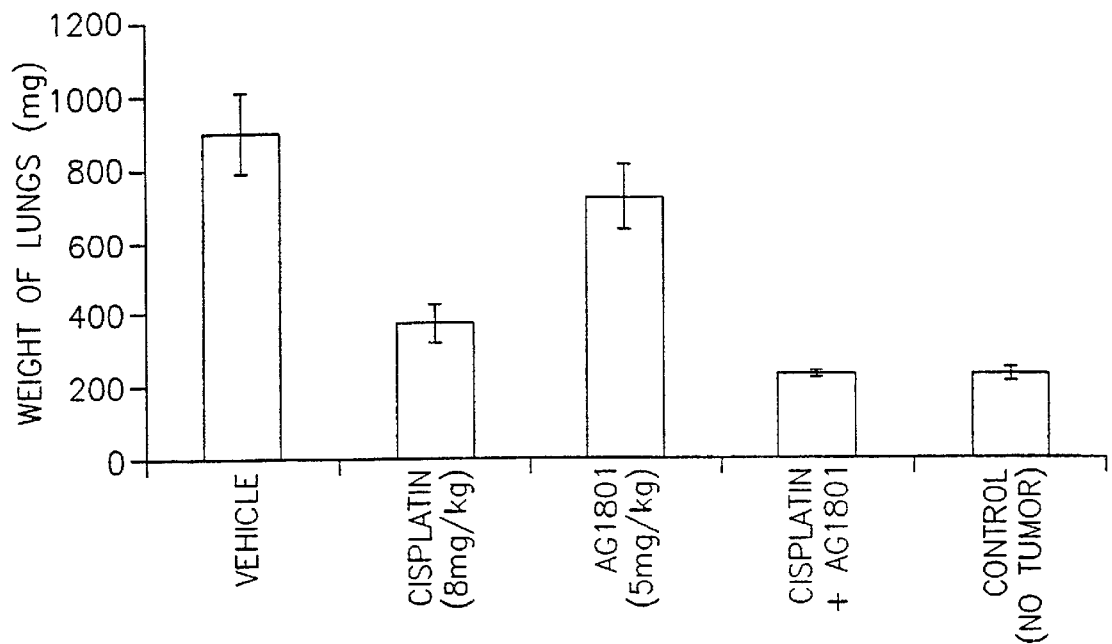
FIG. 25 is a graphic representation showing the weight of lungs in MCA-105 fibrosarcoma tumor bearing mice treated with cisplatin alone, AG1801 alone or a combination of both (FIG. 25A) or with doxorubicin alone, AG1801 alone or their combination (FIG. 25B)
Figure 25B:
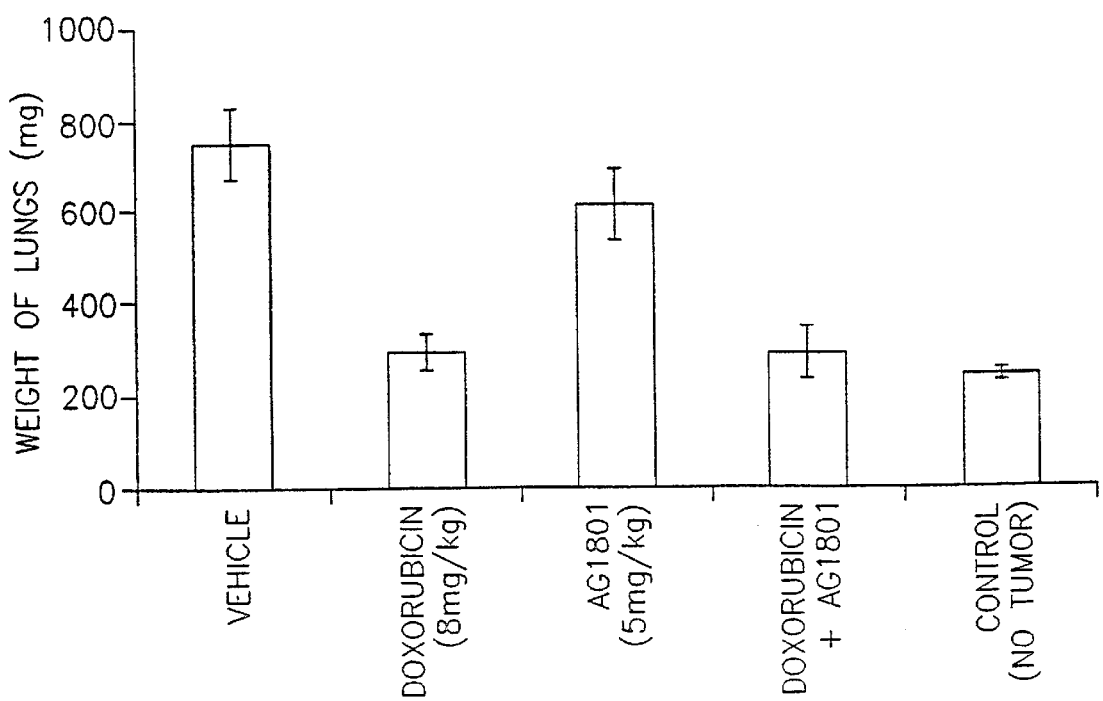

As seen in FIG. 25A and 25B, the weight of the lungs of the tumor bearing mice were significantly higher than that of the control mice. While injection of AG1801 alone had no affect, the injection of cisplatin (FIG. 25A) or doxorubicin (FIG. 25B) reduced the weight of the mice's lungs to a weight similar to that of control non tumor bearing mice. The combined injection of cisplatin and AG1801 (FIG. 25A) and the combined injection of doxorubicin and AG1801 (FIG. 25B) resulted in reduction of tumor load in the lungs of the mice similar to the reduction in the tumor load of mice receiving the cisplatin alone.

The results of the above four examples clearly show that administration of tyrphostins to tumor bearing mice together with cisplatin does not affect the antitumor affect of the cisplatin and in some cases even increases it.

Example 33

The effect of cisplatin and AG1801 on SK-28 human melanoma tumor xenografts in nude mice was determined as explained in Example 29 above.

Figure 26:
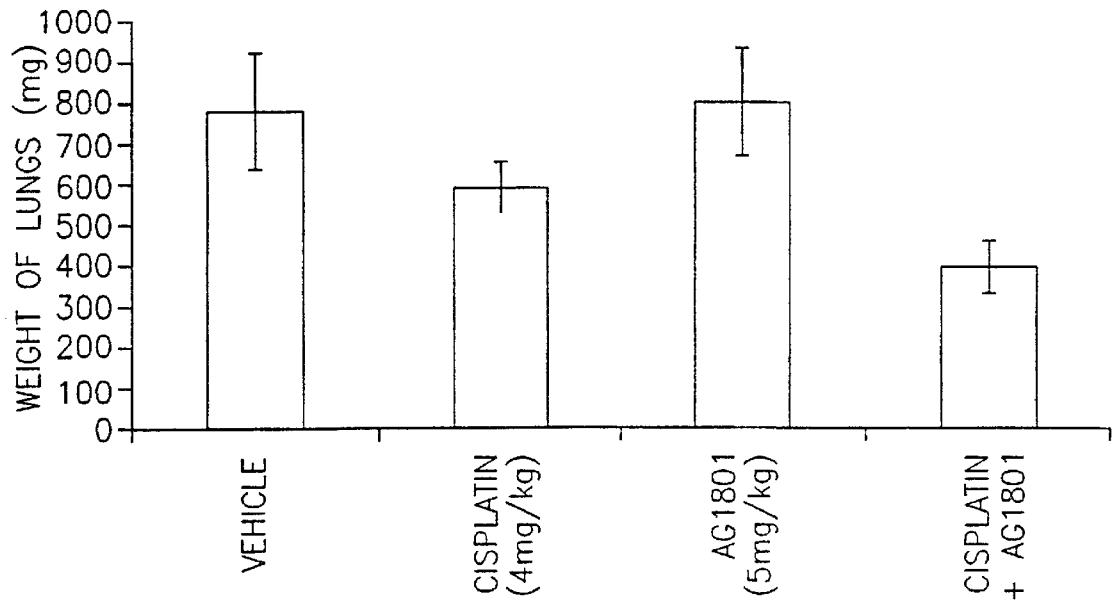
FIG. 26 is a graphic representation showing the weight of lungs of mice treated with cisplatin alone, AG1801 alone or a combination of both.

As seen in FIG. 26, the administration of cisplatin alone reduced the weight of the lungs of the tumor bearing mice to an extent while administration of AG1801 had no therapeutic effect in itself. Combined administration of AG1801 with cisplatin significantly reduced the rate of lungs of the treated mice and thus the administration of AG1801 prior to cisplatin administration enhanced its therapeutic effect.

The above examples clearly show that administration of tyrphostins to tumor bearing mice together with cisplatin or doxorubicin does not impair the anti-tumor effect of the therapeutic agents and in some cases even increases it. Therefore the tyrphostins could be useful in potentiating and intensifying the chemotherapeutic effect of such agents.

VI. The Effect of AG1714 on the Viability of Various Cells in vitro Was Determined as Follows:

Example 34

Murine bone marrow nucleated cells were prepared by gradient centrifugation on histopaque. The cells were then divided into two groups:
  i. Cells incubated for one hour in growth medium alone (control);
  ii. Cells incubated for one hour in growth medium with the addition of various concentrations (5 $\mu$M; 10 $\mu$M or 20 $\mu$M) of the tyrphostin AG 1714.

Cells were then plated on semi-solid agar and the number of colony forming units (CFU) was determined after a 14 day incubation period (see: Nikerich et al., supra, 1986).

Figure 27:
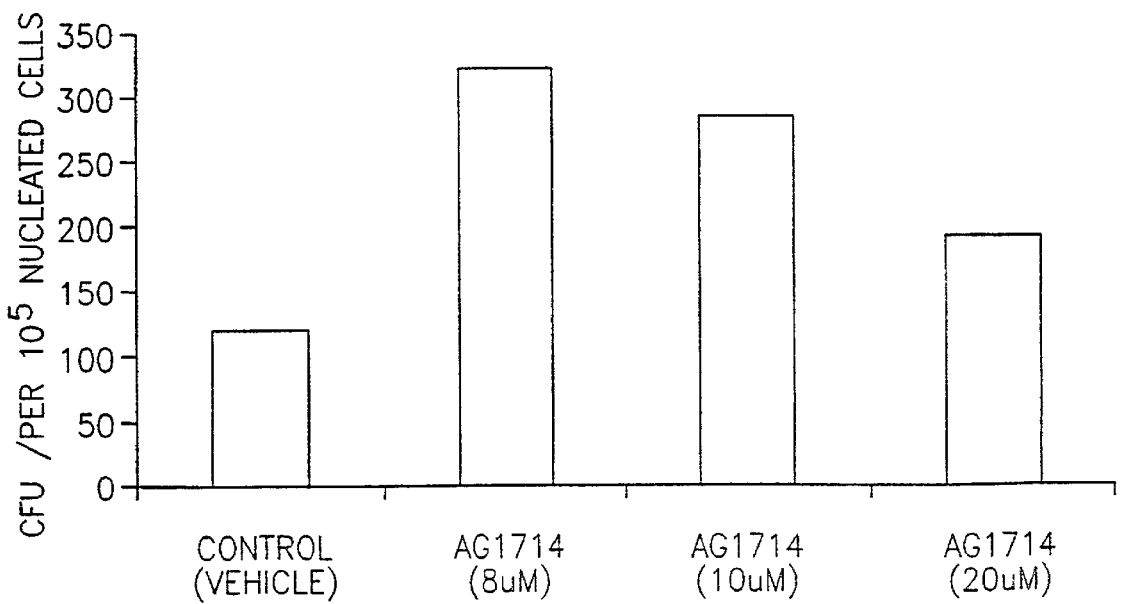
FIG. 27 is a graphic representation showing the number of colony forming units (CFU) in cultures of bone marrow cells grown with or without various concentrations of AG1714.

As seen in FIG. 27, the plating efficiency (determined by the number of CFU per $10^5$ nucleated cells) of the cultures to which AG1714 was added was significantly enhanced as compared to that of the cells grown in growth medium alone. Thus, the tyrphostin AG1714 enables longer preservation of bone marrow cell culture.

Example 35

Thymocytes were prepared from thymuses of young CD1 mice at a concentration of $3 \times 10^6$ cell/ml in RPN11640 growth medium containing 5% FCS. The cells were divided into two groups:
  i. Cells grown in the presence of growth medium alone; and
  ii. Cells grown in growth medium with the addition of AG1714.

The cell viability of the thymocytes in each of the above cultures was determined using the trypsin blue exclusion test at various periods of time after the addition of AG1714 to the cells.

Figure 28:
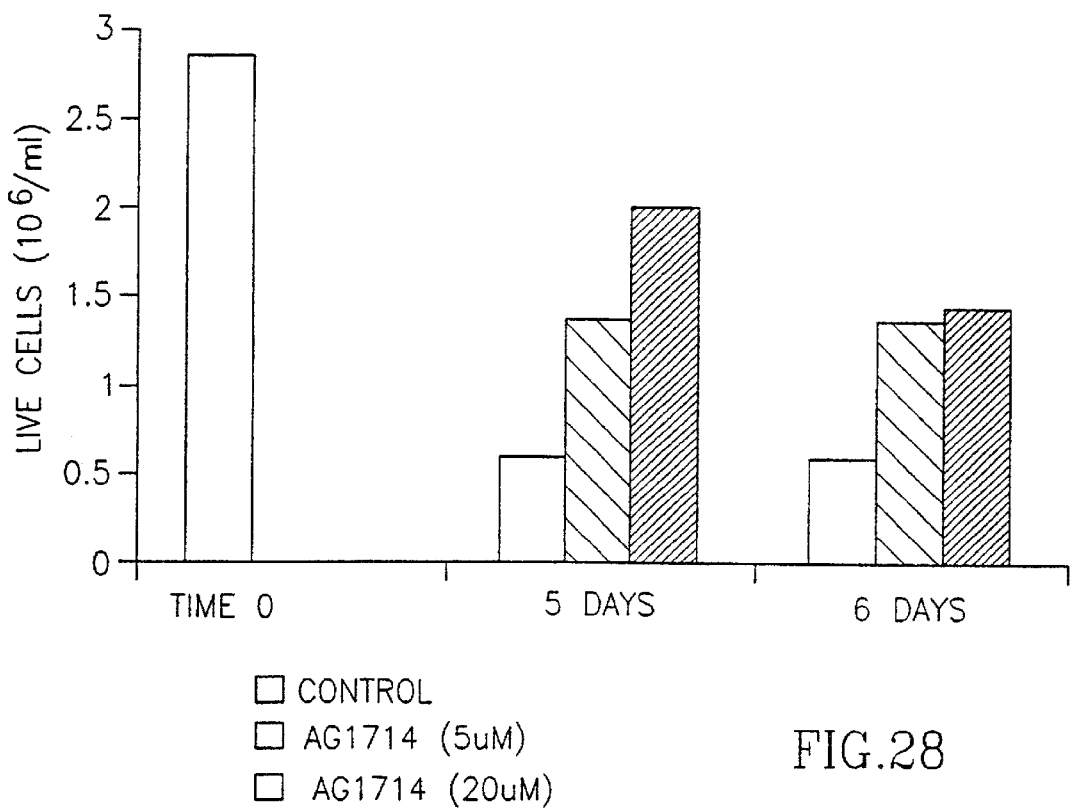
FIG. 28 is a graphic representation showing the viability of thymocytes grown with or without AG1714 at various periods of time after the addition of AG1714 to the cells.

As seen in FIG. 28, addition of AG1714 to the thymocytes in culture significantly enhanced their viability.

Example 36

Primary rat myocyte cultures were prepared from rats as described in Kessler-Iceksan, G., *J. Mol. Cell. Cardiol.*, 20:649-755, 1988. Cardiomyocytes were grown in culture for seven days and then the cultures were divided into two groups:
  i. Cultures grown in growth culture alone;
  ii. Cultures grown in growth culture with the addition of 20 $\mu$M of the tyrphostin AG 1714.

The number of beats per minute of the myocyte clusters in each culture was determined 16 hours and 40 hours after the addition of the tyrphostins to the cells.

Figure 29:
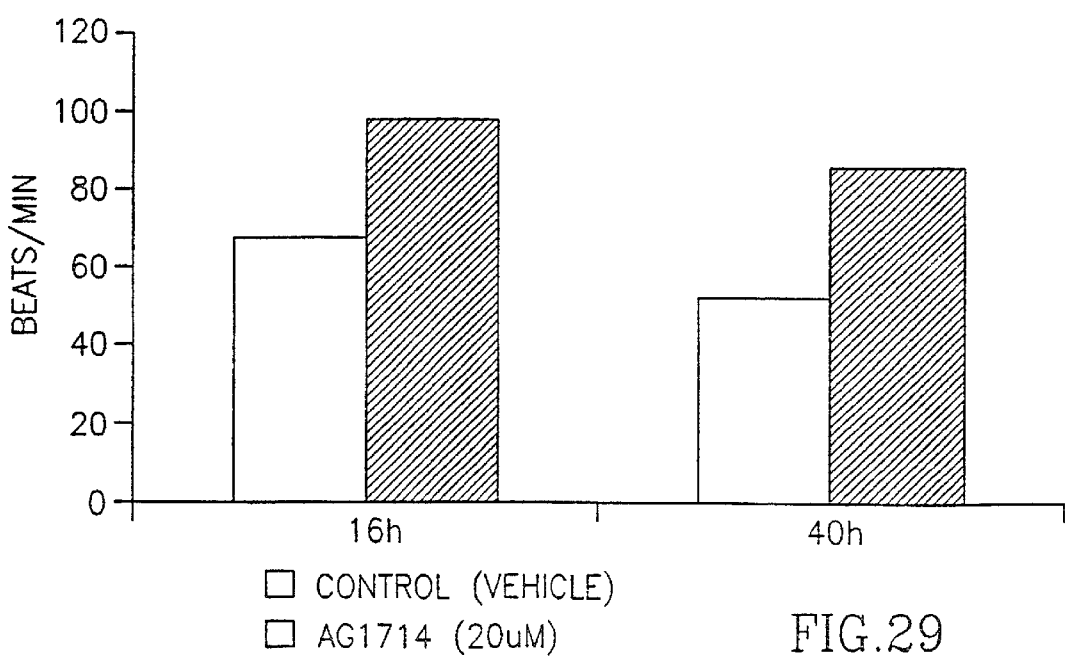
FIG. 29 is a graphic representation showing the number of beats per minute in cardiomyocyte cultures grown with or without AG1714 as an indication of the viability of the cells.

As seen in FIG. 29, the number of beats per minute in the cardiomyocyte cultures to which the tyrphostin AG1714 was added were significantly higher than the number of beats per minute in the cultures grown in the growth medium alone. AG1714 enhanced the viability of the cardiomyocytes in culture.

VII. Toxicity Study of Tyrphostins

Example 37

In order to study the toxic effects of the tyrphostins AG1714 and AG1801, the tyrphostins were injected to ICR mice 3 times a week over a period of five weeks. Each injection contains 20 mls. of the tyrphostins which was prepared in the vehicle propylene carbonate:cremophore (40/60) diluted 1:20 with saline/bicarbonate.

In order to test the toxic effect of the cumulative administration of the tyrphostins, various parameters of the injected mice were determined including their weight, weight of their internal organs (thymus, spleen, kidney), full blood chemistry, number of bone marrow cells, etc.

As seen in Table 7 below, injection of the tyrphostins AG1714 and AG1801 caused no significant changes in the parameters tested in the injected mice as compared to the same parameters in control mice injected with saline or the vehicle only. Therefore, no toxic effects of the tyrphostins were apparent following their cumulative administration to mice. In addition, injection of the tyrphostins caused no mortality of the mice.

TABLE 7

Subchronic intraperitoneal administration of AG1714 and AG1801
(ICR female mice, injection 3 times a week, 5 weeks)

|  | Control 1 Saline | Control 2 Vehicle | AG1714 20 mg/kg × 15 | AG1801 5 mg/kg + 15 |
|---|---|---|---|---|
| Weight (g) |  | 29.3 ± 3.1 | 28.6 ± 2.3 | 29.1 ± 1.7 |
| Thymus (mg) |  | 50.2 ± 7.7 | 53.8 ± 12.3 | 57 ± 9.3 |
| Spleen (mg) |  | 118 ± 27 | 136 ± 16 | 119 ± 19.6 |
| Kidney (mg) |  | 176 ± 21 | 162 ± 12 | 164 ± 9.8 |
| Leukoc. (k/ul) | 6.1 ± 2.3 | 5.5 ± 0.98 | 4.9 ± 2.3 | 6.8 ± 3.3 |
| Lymph. (%) | 88.1 ± 2.35 | 83.3 ± 4.12 | 81.5 ± 2.35 | 80.4 ± 6.1 |
| Neutr. (%) |  | 4.2 ± 1.4 | 4.2 ± 1.2 | 5.3 ± 1.2 |
| Monoc. (%) |  | 10.6 ± 2.6 | 11.9 ± 1.3 | 12.3 ± 5.2 |
| Eosin. (%) |  | 0.2 ± 0.1 | 0.1 ± 0.05 | 0.3 ± 0.23 |
| Basoph. (%) |  | 0.22 ± 0.08 | 0.24 ± 0.11 | 0.3 ± 0.07 |
| RBC (M/ul) |  | 8.4 ± 0.33 | 9.0 ± 0.33 | 8.4 ± 0.3 |
| HGB (g/dl) | 14.0 ± 2.5 | 14.2 ± 0.5 | 14.9 ± 0.56 | 14.5 ± 0.67 |
| PLT (K/ul) | 1236 ± 176 | 1229 ± 12.7 | 1475 ± 252 | 1309 ± 304 |
| Glucose (mg/dl) | 147 ± 11.3 | 177 ± 24 | 144 ± 17 | 177 ± 20.5 |
| BUN (mg/dl) | 22 ± 4.4 | 21 ± 2.9 | 25.2 ± 3.3 | 24.2 ± 2.2 |
| Creatinine (mg/dl) | 0.4 ± 0.0 | 0.42 ± 0.04 | 0.46 ± 0.05 | 0.42 ± 0.04 |
| Total Prot. (g/dl) | 5.4 ± 0.17 | 5.6 ± 0.2 | 5.8 ± 0.2 | 5.6 ± 0.08 |
| Albumin (g/dl) | 3.1 ± 0.0 | 3.1 ± 0.09 | 3.2 ± 0.13 | 3.1 ± 0.07 |
| Calcium (mg/dl) | 9.9 ± 0.4 | 9.9 ± 0.26 | 9.9 ± 0.3 | 9.8 ± 0.36 |
| In. Phosph. (mg/dl) | 8.5 ± 0.7 | 8.0 ± 0.75 | 8.4 ± 0.43 | 7.9 ± 1.1 |
| Uric acid (mg/dl) | 1.1 ± 0.21 | 2.0 ± 0.44 | 1.8 ± 0.18 | 2.0 ± 0.36 |
| Total Bilirub. (mg/dl) | 0.23 ± 0.06 | 0.2 ± 0.0 | 0.2 ± 0.0 | 0.2 ± 0.0 |
| Alk. Phosph. (U/l) | 110 ± 23.8 | 79 ± 17 | 67 ± 12.8 | 69.6 ± 0.26 |
| LHD (U/l) | 545 ± 157 | 996 ± 235 | 960 ± 226 | 972 ± 238 |
| GOT (U/l) | 67 ± 11 | 71.4 ± 6.5 | 70 ± 18 | 68 ± 12 |

TABLE 7-continued

Subchronic intraperitoneal administration of
AG1714 and AG1801
(ICR female mice, injection 3 times a week, 5 weeks)

|  | Control 1 Saline | Control 2 Vehicle | AG1714 20 mg/kg × 15 | AG1801 5 mg/kg + 15 |
|---|---|---|---|---|
| GPT (U/l) | 30 ± 4.6 | 28.8 ± 3.1 | 25.6 ± 4.2 | 28 ± 5.5 |
| CPK (U/l) | 461 ± 179 | 604 ±0 115 | 659 ± 486 | 582 ± 127 |
| Amylase (U/l) | 2451 ± 176 | 2211 ± 352 | 2392 ± 230 | 2169 ± 222 |
| Cholester. (mg/dl) | 115 ± 25 | 98.8 ± 17.5 | 99 ± 5.7 | 90 ± 6.1 |
| Triglycer. (mg/dl) | 216 ± 84 | 125 ± 7.9 | 155 ± 54 | 138 ± 50 |
| Nuclear BM cells × 10$^6$ | 16.3 ± 0.7 | 15.2 ± 2.0 | 18.6 ± 3.6 | 16.5 ± 0.87 |
| Colonies (in femur) |  | 12790 ± 1620 | 17600 ± 2590 | 15690 ± 2040 |
| Clusters (in femur) |  | 8170 ± 697 | 15000 ± 2140 | 13410 ± 1740 |

Vehicle - Propylene carbonate: Cremophore (40:60)
Diluted 1:20 with saline/bicarbonate VIII. Inhibition of Immune Specific Activities

Example 38

Murine peritoneal exudate cytotoxic lymphocytes (PEL) capable of specific lysis of EL-4 cells were prepared and tested as described in Lavy, R. et al., *J. Immunol.* 154:5039–5048, 1995. The EL-4 cells were divided into cells which were incubated with PELs alone, cells which were incubated with AG1714 (20 μM) and then with PELs and cells which were incubated with AG1714 (50 82 M) and then with PELs. The lysis of the target EL-4 cells was determined using the specific $^{51}$Cr release assay.

Figure 30:
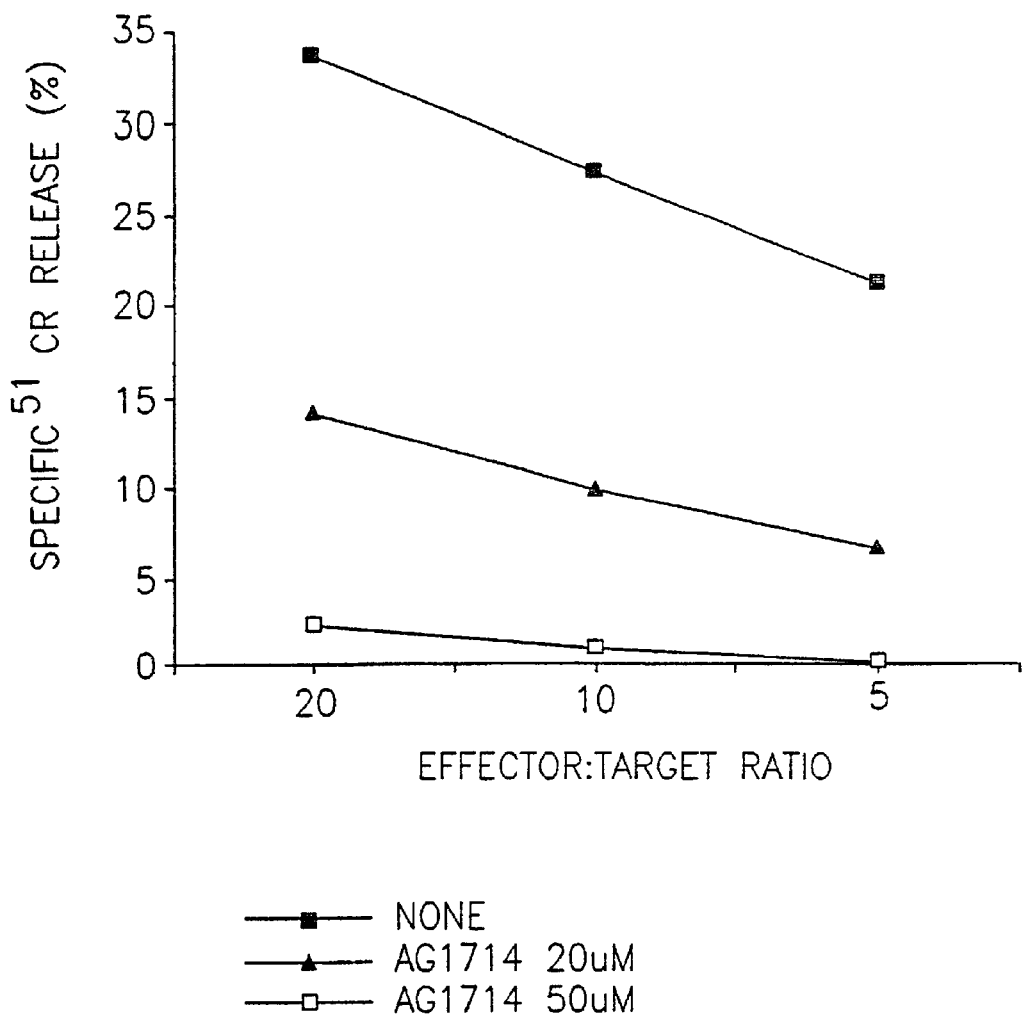
FIG. 30 is a graphic representation showing the percent lysis measured by percent of specific $S^{51}$ Cr release of target EL-4 cells by murine peritoneal exudate cytotoxic lymphocytes (PEL) in the presence or absence of AG1714.

As seen in FIG. 30, addition of AG1714 reduced the specific cytotoxic activity of PELs against the target EL-4 cells. The inhibitive effect of AG1714 was dose dependent.

The above results indicate that tyrphostins may be useful for reducing immune mediated rejection of transplants, in cases of autoimmunity and in conditions involving specific immune activity against cells (e.g. anti-CD4 cells such as in the case of AIDS).

IX. Anti-inflammatory Effect of Tyrphostins

One of the main complications of an inflammatory reaction in an individual is the development of septic shock which results from over effects of the immune reaction which is mediated mainly be cytokines such as TNF and IL-1. The involvement of tyrphostins in TNF and IL-1 related immune responses was determined as follows:

Example 39

A. Incubation of mouse fibroblastic cells with TNF-α result in apoptosis of these cells. In order to test the effect of tyrphostins on the TNF-α-induced apoptosis of the cells, A9 mouse fibroblastic cells were incubated for two hours with cycloheximide (50 μg/ml) after which the various tyrphostins were added at a final concentration of 20 μM except AG1801 that was added at the final concentration of 5 μM. Following one hour incubation with the tyrphostins, TNF-α was added to the cells at a concentration of 0.2 ng/ml and the cells were incubated for an additional ten hours. At the end of ten hours, the cell cultures were analyzed by FACS using propidium iodide and the extent of apoptosis in each of the cell cultures (seen as DNA fragmentation) was determined (see Novogrodsky, A., et al., *Science*, 264:1319-1322, 1994).

As seen in Table 8 below, addition of the various tyrphostins to the mouse fibroblastic cells incubated with TNF, reduced the apoptopic effect of TNF significantly. The extent of the reduction of the apoptopic effect of TNF by the various tyrphostins was slightly different.

TABLE 8

Prevention of TNF-α-induced apoptosis
of mouse fibroblastic cells (A-9) by tyrphostins

| Tyrphostins* | Apoptosis (%) TNF-α (0.2 ng/ml) | |
|---|---|---|
|  | − | + |
| None (vehicle) | 9.3 | 28.7 |
| AG1714 | 4.5 | 9.9 |
| AG1801 | 6.6 | 10.2 |
| AG126 | 8.3 | 19.4 |
| AG1802 | 7.6 | 17.2 |

*All tyrphostins were added at a final concentration of 20 μM, except AG1801, that was added at a final concentration of 5 μM B. As seen in Table 9, cell cycle analysis of the above cell cultures showed that treatment of the cells with TNF-α induced a $G_1$ arrest. There was a direct correlation between the tyrphostins' reduction of the apoptotic effect caused by TNF and their ability to prevent $G_1$ arrest in the cell cultures.

TABLE 9

Prevention by AG1714 of TNF-α- induced Go/G1 arrest
and apoptosis in mouse fibroblastic cells (A-9)

|  | Cell cycle % | | | Apoptosis % |
|---|---|---|---|---|
|  | G1 | S | G2 + M |  |
| Control | 60.8 | 36.2 | 3.0 | 9.3 |
| TNF-α (0.2 ng/ml) | 85.8 | 7.6 | 6.6 | 28.7 |
| AG1714 (30 μM) | 58.1 | 38.1 | 3.8 | 4.5 |
| TNF-α + AG1714 | 64.5 | 31.2 | 4.3 | 9.9 |

Example 40

The effect of tyrphostins on TNF-induced cytotoxicity was determined in vitro using A-9 cells as described in Example 39 above. In addition, the effect of tyrphostin on TNF mediated cytotoxicity in vivo was determined in mice injected with LPS (which induces TNF toxicity in vivo). *E. coli* LPS the concentration of 1.3 mg/mouse was injected i.p. to CD1 mice. While control mice were injected in addition with the vehicle only, the remaining mice were injected with the various tyrphostins (20 mg/kg) i.p. two hours prior to LPS injection. As seen in Table 10A, in agreement with the results shown in Example 39 above, addition of tyrphostins to the cells incubated with TNF significantly reduces the cytotoxic effect of TNF. As seen in Table 10B, most of the tyrphostins showed a significant protective effect against the LPS-induced toxicity in vivo which correlated with their activity in vitro.

TABLE 10

Effect of tyrphostins on TNF - induced cytotoxicity (in vitro)
and LPS - induced lethal toxicity (in vivo)

A
in vitro, (live cells, % of control) TNF

| AG (20 μM) | None | 0.05 ng/ml | 0.2 ng/ml | 1.0 ng/ml |
|---|---|---|---|---|
| Control | 100 | 41 | 19 | 6 |
| AG1714 | 119 | 102 | 90 | 62 |

TABLE 10-continued

Effect of tyrphostins on TNF - induced cytotoxicity (in vitro) and LPS - induced lethal toxicity (in vivo)

| | | | | |
|---|---|---|---|---|
| AG1719 | 102 | 83 | 58 | 41 |
| AG26 | 107 | 86 | 64 | 31 |
| AG126 | 107 | 75 | 49 | 33 |
| AG1641 | 102 | 70 | 41 | 21 |
| AG1720 | 104 | 53 | 26 | 11 |

B
in vivo

| alive/total | % alive mice |
|---|---|
| 4/10 | 40 |
| 5/5 | 100 |
| 4/5 | 80 |
| 4/5 | 80 |
| 4/5 | 80 |
| 3/5 | 60 |
| 2/5 | 40 |

Example 41

IL-1 is one of the main mediators of septic shock in vivo. In order to determine the inhibitive activity of AG1714 on production of IL-1 from cells incubated with LPS, human peripheral blood monocytes (PBM) at a concentration of $2\times10^6$ cells/ml were divided into the following groups:

i. Cells grown in growth medium alone;
ii. Cells grown in growth medium to which AG1714 was added (20 $\mu$M);
iii. Cells grown in growth medium to which LPS was added (10 mg/ml); and
iv. Cells grown in growth medium with the addition of LPS (10 mg/ml) and AG1714 (20,$\mu$M). The cells were incubated for 24 hours and the amount of IL-1$\beta$ was determined using the Genzyme ELISA kit.

As seen in Table 11, which shows two experiments carried out as described above, addition of AG1714 to cells incubated with LPS significantly reduced the amount of IL-1$\beta$ produced by the cells.

TABLE 11

Inhibition by AG1714 of LPS-induced IL-1$\beta$ production in human peripheral mononuclear cells

| | | IL-1$\beta$ pg/ml AG1714 (20 $\mu$M) | |
|---|---|---|---|
| Exp. 1 | | − | + |
| | None | 2522 | 1174 |
| | LPS (10 $\mu$g/ml) | 10187 | 1230 |
| Exp. 2 | | − | − |
| | None | 583 | 648 |
| | LPS (10 $\mu$g/ml) | 9309 | 970 |

The above results indicate that tyrphostins may be useful in reducing the non desired IL-1 mediated effect involved in septic shock.

The results of the above three examples indicate that tyrphostins may be useful in reducing or preventing the development of septic shock during an inflammatory response. The tyrphostins may also be useful as anti-inflammatory agents and in counteracting pathogenetic effects mediated by various cytokines (e.g. TNF and IL-1) which occur for example in autoimmunity.

What is claimed is:

1. A method of treatment of an individual, for countering damage to cells, tissue or organ, said method comprising administering to the individual an effective amount of a compound of the general formula

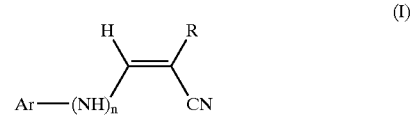

(I)

wherein
Ar is a group of the formulae

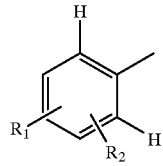

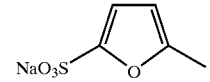

(ii)

n is 0 or, when Ar has the formula (i) above, then n may be 1,
R is CN, —C(S)NH$_2$, —C(O)NHR$_3$ or, when Ar is a group of formula (i) in which R$_1$ is 4-NO$_2$ and R$_2$ is H or 3-OH, then R may also be a group of the formula

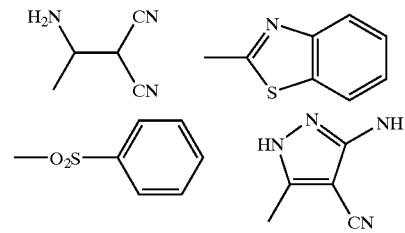

wherein R$_3$ is H, phenyl, phenyl (lower alkyl) or pyridylmethyl;
R$_1$ and R$_2$ are each independently H, OH, NO$_2$ or, when R is CN, also CH$_3$, F, or CF$_3$, provided that when Ar is the group of formula (i):
a) R$_1$ represents 4-NO$_2$; and
b) when R is —CN, —C(O)NHCH$_2$C$_6$H$_5$ or a group of the formula:

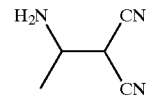

then R$_2$ cannot represent OH, together with a pharmaceutically effective carrier.

2. A method according to claim 1, wherein in the compound of formula I, R is CN, —C(S)NH$_2$, —C(O)NHCH$_2$C$_6$H$_5$ or a group of the formula

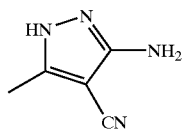

and n is 0, $R_1$ is 4-$NO_2$ and $R_2$ is H.

3. A method according to claim 1, wherein said damage is caused by a cytotoxic drug.

4. A method according to claim 3, wherein the cytotoxic drug is an anti-neoplastic drug.

5. A method according to claim 4, wherein the cytotoxic drug is selected from the group consisting of cisplatin, doxorubicin, cyclophosphamide, mitomycin-C and 5-fluorouracil.

6. A method according to claim 1, for countering myelotoxicity or lymphotoxicity.

7. A method according to claim 1, wherein the damage is a result of undesired harmful effects of irradiation treatment.

8. A method according to claim 1, wherein the compound of formula I is administered in combination with a cytotoxic drug or an irradiation treatment.

9. A method according to claim 8, wherein the compound of formula I is administered prior to the administration of the cytotoxic drug or the irradiation treatment.

10. A method according to claim 1, wherein the compound of formula I is administered intravenously.

11. A method according to claim 1, wherein the compounds of formula I is administered orally.

12. A method according to claim 1, wherein the damage is caused by an immune mediated or inflammatory response.

13. A method for ex vivo preservation of organ, tissue or cells comprising contacting the organ, tissue or cells ex vivo with a compound of the general formula

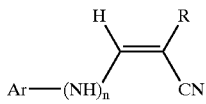

(I)

wherein:
Ar is a group of the formulae

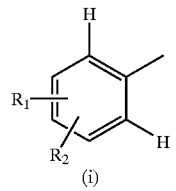

(i)

or

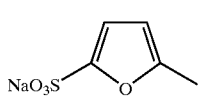

(ii)

n is 0 or, when Ar has the formula (i) above, then n may also be 1,

R is CN, —C(S)$NH_2$, —C(O)$NHR_3$ or, when $R_1$ is 4-$NO_2$ and $R_2$ is H or 3-OH, then R may also be a group of the formula

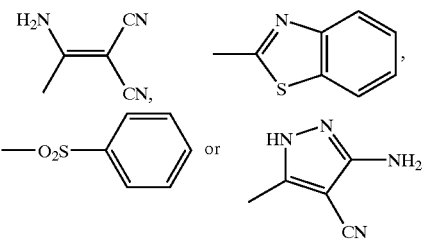

where $R_3$ is H, phenyl, phenyl(lower alkyl) or pyridylmethyl;

$R_1$ and $R_2$ are each independently H, OH, $NO_2$ or, when R is CN, also $CH_3$, F, or $CF_3$, provided that both $R_1$ and $R_2$ are not simultaneously H, together with a pharmaceutically acceptable carrier.

* * * * *